US011026604B2

United States Patent
Chen et al.

(10) Patent No.: US 11,026,604 B2
(45) Date of Patent: Jun. 8, 2021

(54) MEDICAL MONITORING DEVICE FOR HARMONIZING PHYSIOLOGICAL MEASUREMENTS

(71) Applicant: Cercacor Laboratories, Inc., Irvine, CA (US)

(72) Inventors: Jesse Chen, Foothill Ranch, CA (US); Sean Merritt, Lake Forest, CA (US); Cristiano Dalvi, Lake Forest, CA (US); Ferdyan Lesmana, Irvine, CA (US); Hung The Vo, Fountain Valley, CA (US); Kevin Hughes Pauley, Lake Forest, CA (US); Jeroen Poeze, Rancho Santa Margarita, CA (US); Ruiqi Long, Irvine, CA (US); Stephen L. Monfre, Rancho Santa Margarita, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 185 days.

(21) Appl. No.: 16/034,743

(22) Filed: Jul. 13, 2018

(65) Prior Publication Data
US 2019/0015023 A1    Jan. 17, 2019

Related U.S. Application Data

(60) Provisional application No. 62/532,273, filed on Jul. 13, 2017, provisional application No. 62/667,983, filed on May 7, 2018.

(51) Int. Cl.
*A61B 5/02*      (2006.01)
*A61B 5/145*     (2006.01)
(Continued)

(52) U.S. Cl.
CPC ........ *A61B 5/14532* (2013.01); *A61B 5/0075* (2013.01); *A61B 5/0205* (2013.01);
(Continued)

(58) Field of Classification Search
CPC . A61B 5/14532; A61B 5/7278; A61B 5/7203; A61B 5/0205; A61B 5/0075;
(Continued)

(56) References Cited

U.S. PATENT DOCUMENTS 4,960,128 A    10/1990   Gordon et al.
4,964,408 A    10/1990   Hink et al.
(Continued)

FOREIGN PATENT DOCUMENTS

EP    3056141         8/2016
PL    3056141 A1  *   8/2016

OTHER PUBLICATIONS

International Search Report and Written Opinion, re PCT Application No. PCT/US2018/042148, dated Nov. 19, 2018.

*Primary Examiner* — Rex R Holmes
(74) *Attorney, Agent, or Firm* — Knobbe, Martens, Olson & Bear, LLP

(57) ABSTRACT

Systems, methods, apparatuses, and medical devices for harmonizing data from a plurality of non-invasive sensors are described. A physiological parameter can be determined by harmonizing data between two or more different types of non-invasive physiological sensors interrogating the same or proximate measurement sites. Data from one or more first non-invasive sensors can be utilized to identify one or more variables that are useful in one or more calculations associated with data from one or more second non-invasive sensors. Data from one or more first non-invasive sensors can be utilized to calibrate one or more second non-invasive sensors. Non-invasive sensors can include, but are not limited to, an optical coherence tomography (OCT) sensor, a bio-impedance sensor, a tissue dielectric constant sensor, a plethysmograph sensor, or a Raman spectrometer.

22 Claims, 18 Drawing Sheets

(51) Int. Cl.
  *A61B 5/00* (2006.01)
  *A61B 5/0205* (2006.01)
  *A61B 5/026* (2006.01)
  *A61B 5/0295* (2006.01)
  *A61B 5/0531* (2021.01)
  *A61B 5/107* (2006.01)
  *A61B 5/1455* (2006.01)

(52) U.S. Cl.
  CPC .......... *A61B 5/7203* (2013.01); *A61B 5/7278* (2013.01); *A61B 5/0066* (2013.01); *A61B 5/0261* (2013.01); *A61B 5/0295* (2013.01); *A61B 5/0531* (2013.01); *A61B 5/1075* (2013.01); *A61B 5/1079* (2013.01); *A61B 5/14551* (2013.01); *A61B 5/442* (2013.01); *A61B 5/443* (2013.01); *A61B 2560/0223* (2013.01); *A61B 2576/02* (2013.01)

(58) Field of Classification Search
  CPC ................ A61B 5/442; A61B 2576/02; A61B 2560/0223; A61B 5/443; A61B 5/14551; A61B 5/1079; A61B 5/1075; A61B 5/0531; A61B 5/0295; A61B 5/0261; A61B 5/0066
  See application file for complete search history.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |

(56) References Cited

U.S. PATENT DOCUMENTS

| | | |
|---|---|---|
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |

(56) References Cited

U.S. PATENT DOCUMENTS

| | | |
|---|---|---|
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |

(56) References Cited

U.S. PATENT DOCUMENTS

| | | |
|---|---|---|
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |

(56) References Cited

U.S. PATENT DOCUMENTS

| | | |
|---|---|---|
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,759,714 B2 | 9/2017 | Bordelon et al. |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |

(56) References Cited

U.S. PATENT DOCUMENTS

| | | |
|---|---|---|
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2006/0200017 A1 | 9/2006 | Monfre et al. |
| 2006/0211926 A1 | 9/2006 | Yu et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0188538 A1* | 7/2012 | Patil .................. G01N 21/4795 356/301 |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0090537 A1 | 4/2013 | Schemmann et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0354015 A1 | 12/2016 | Zhang et al. |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |

(56) References Cited

U.S. PATENT DOCUMENTS

| | | |
|---|---|---|
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0100064 A1* | 4/2017 | Van Dorpe ............ G01N 21/65 |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188864 A1* | 7/2017 | Drury ................ A61B 5/02427 |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0103874 A1 | 4/2018 | Lee et al. |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0199871 A1 | 7/2018 | Pauley et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |

\* cited by examiner

MEDICAL MONITORING DEVICE FOR HARMONIZING PHYSIOLOGICAL MEASUREMENTS

CROSS-REFERENCE TO RELATED APPLICATIONS

The present application claims priority benefit to U.S. Provisional Application No. 62/532,273, entitled "MEDICAL MONITORING DEVICE FOR COORDINATING PHYSIOLOGICAL MEASUREMENTS," filed Jul. 13, 2017, and U.S. Provisional Application No. 62/667,983, entitled "MEDICAL MONITORING DEVICE FOR HARMONIZING PHYSIOLOGICAL MEASUREMENTS," filed May 7, 2018, each of which is hereby incorporated herein by reference in its entirety.

TECHNICAL FIELD

The present disclosure relates to blood glucose determination in biological tissues. Specifically, this disclosure relates to systems, methods, and apparatuses for harmonizing data from a plurality of non-invasive sensors to estimate blood glucose levels.

BACKGROUND

Monitoring of blood glucose (blood sugar) concentration levels has long been critical to the treatment of diabetes in humans. Current blood glucose monitors involve a chemical reaction between blood serum and a test strip, requiring an invasive extraction of blood via a lancet or pinprick. Small handheld monitors have been developed to enable a patient to perform this procedure anywhere, at any time. But the inconvenience of this procedure—specifically the blood extraction and the use and disposition of test strips—has led to a low level of compliance. Such low compliance can lead to serious medical complications. Thus, a non-invasive method for monitoring blood glucose is needed.

SUMMARY

The present disclosure describes example systems, methods, apparatuses, and medical devices for harmonizing data from a plurality of non-invasive sensors. In general, a physiological parameter can be determined by harmonizing data between two or more different types of non-invasive physiological sensors interrogating the same or proximate measurement sites. In some cases, data from one or more first non-invasive sensors can be utilized to identify one or more variables that are useful in one or more calculations associated with data from one or more second non-invasive sensors. In some cases, data from one or more first non-invasive sensors can be utilized to calibrate one or more second non-invasive sensors. Non-invasive sensors can include, but are not limited to, an optical coherence tomography (OCT) sensor, a bio-impedance sensor, a tissue dielectric constant sensor, a plethysmography sensor, or a Raman spectrometer.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

BRIEF DESCRIPTION OF THE DRAWINGS

The following drawings and the associated descriptions are provided to illustrate embodiments of the present disclosure and do not limit the scope of the claims.

Figure 1:
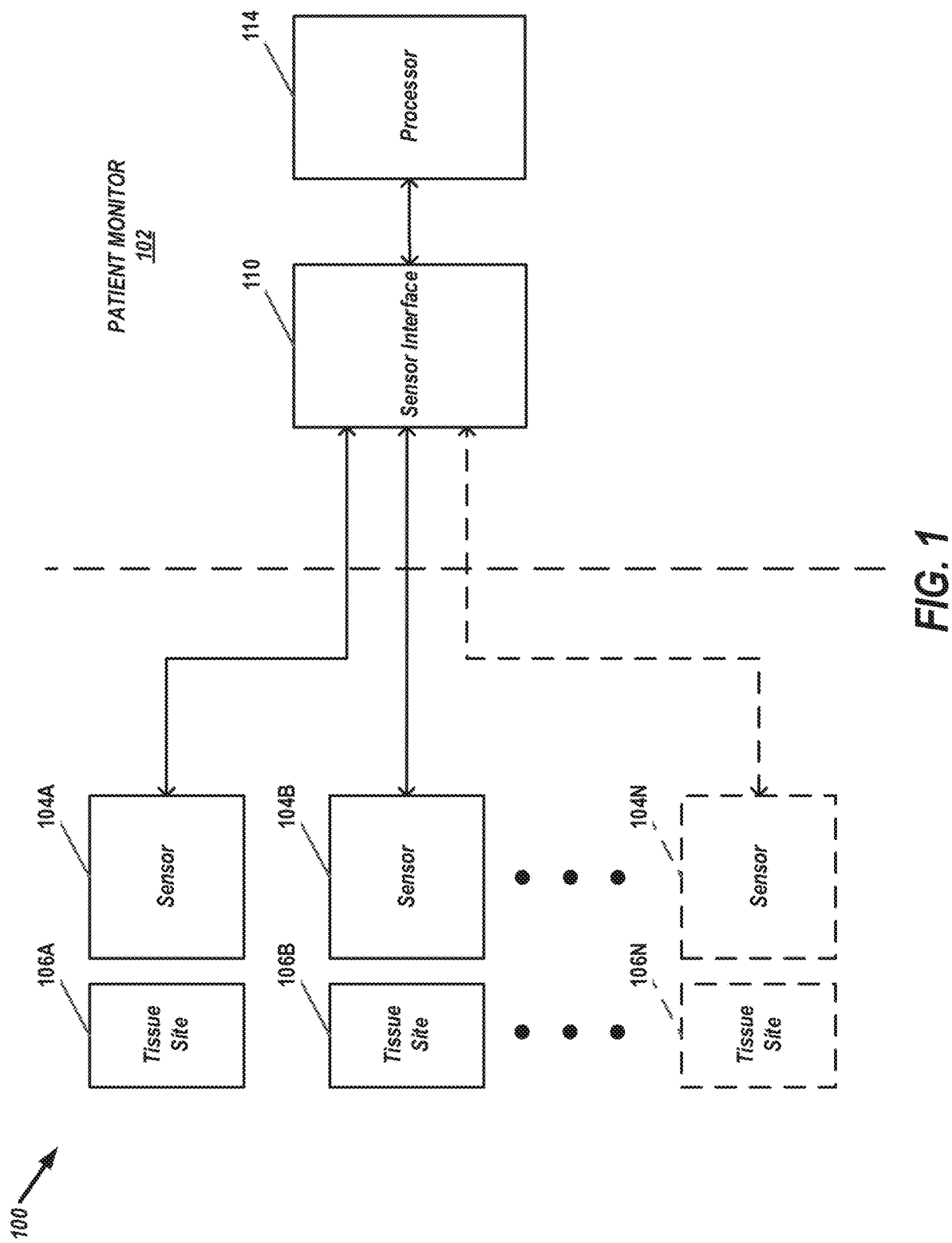
FIG. 1 illustrates an example patient monitoring system that includes a plurality of physiological sensors.

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

Overview

Many non-invasive techniques for determining blood glucose have significant shortcomings, such as low accuracy (for example, less accuracy than invasive home monitors) and insufficient specificity of glucose concentration measurement. Accordingly, there is a need for an improved method to non-invasively monitor glucose. Systems and methods disclosed herein address various challenges related to non-invasively determining a patient's blood glucose level by harmonizing data from multiple non-invasive sensors. Each of the non-invasive sensors can interrogate the same or a similar tissue site of a patient, and variables identified using one or more sensors can be utilized to improve data from one or more other sensors. Using these data harmonization techniques, a glucose concentration measurement can be obtained.

In many instances, a single non-invasive sensor may lack the functionality to measure each of the parameters required for an accurate determination of an analyte concentration. As a result, many physiological monitoring techniques include estimations, such as those based on common assumptions, to compensate for the lack of known data. However, due to the sensitivity of analyte measurements, these estimations can result in inaccurate or unreliable determinations.

For example, Beer's Law (also known as the Beer-Lambert Law) relates the attenuation of light to properties of a material. In particular, Beer's law states that absorbance of a material is proportional to the concentrations of the attenuating species in the material sample. The relationship between these parameters is expressed in Equation 1 below:

$$A = \varepsilon * b * c \quad \text{(Equation 1)}$$

where A is the absorbance of the material at a given wavelength of light, $\varepsilon$ is the molar absorptivity or extinction coefficient (L mol$^{-1}$ cm$^{-1}$), unique to each molecule and varying with wavelength, b is the length of the light path through the material (cm), and c is the concentration of an analyte of interest (mol L$^{-1}$).

In many cases, the length of the light path through the material (sometimes referred to as the path length) is estimated. For example, a generic finger may be associated with a first estimated path length value, while a generic nose may be associated with a second path length value. However, every person has a unique tissue geometry, which can include, but is not limited to, unique skin structure or skin thickness. Furthermore, because tissue is not uniform throughout a person's body, even tissue sites that are close in proximity, such as two different measurements sites on a patient's finger, can have a different tissue geometry. As noted above, a specific tissue geometry of a particular tissue site can affect the path length value. Accordingly, a non-invasive physiological sensor can be configured to obtain skin geometry data, which can be utilized to calculate a path length associated with a tissue site. In addition or alternatively, the skin geometry data can be utilized to calibrate one or more sensors (for example, select a focal depth of Raman spectrometer), which can result in more accurate analytes measurements, such as blood glucose concentration measurements.

An optical coherence tomography, or OCT, sensor can be utilized to obtain tissue geometry information. OCT is an optical imaging technique using light waves that produce high-resolution imagery of biological tissue. OCT creates its images by interferometrically scanning in depth a linear succession of spots, and measuring backscattered light at different depths in each successive spot. The OCT data can be processed to present an image of the linear cross section. OCT data can be processed to determine tissue geometry information, such as skin geometry. For example, the OCT data can provide data regarding a thickness of one or more skin layers, such as the epidermis, the dermoepidermal junction, or the dermis.

In addition or alternatively, OCT data can be utilized to determine whether successive OCT measurements have occurred in the same or a different location. For example, one reason data harmonization between sensors is available relates to the specific optical profile of a particular tissue site. That is, a particular tissue site retains its specific optical profile, and a different measurement location may have a different optical profile. Thus, in many cases, to maintain data harmonization capabilities, each of the sensors should interrogate the same or a substantially proximate tissue site. One problem associated with interrogating the same or a substantially proximate tissue site relates to the subsequent placement of a sensor after it has been removed from the patient. To solve these and other problems, tissue geometry information associated with OCT data can be utilized to determine whether a later one of successive OCT measurements is taken at the same tissue site as a previous one of the successive OCT measurements.

A bio-impedance or tissue dielectric constant sensor can be utilized to obtain tissue geometry information. For example, bio-impedance or tissue dielectric constant data can provide information relating to one or more skin layers, a hydration of one or more skin layers, or a cellular structure of the tissue.

Raman spectroscopy has exhibited promise with respect to blood glucose detection, for example, due to its capability to gain information about the molecular constitution non-invasively. For example, features such as peaks of the Raman spectra are considered the Raman "fingerprints" of analytes such as glucose. Accordingly, using an isolated or semi-isolated Raman signal, the system can identify physiological data, such as information regarding a patient's blood glucose level.

For various reasons, it has been challenging to isolate a pure Raman signal from a signal obtained from a Raman spectrometer. For example, emission of fluorescence in tissue often overwhelms any signal collected from the Raman spectrometer, thereby hiding Raman features. In addition, attenuation of the signal due to absorption can further affect prediction of analytes using the collected signal. Furthermore, varying tissue geometries at tissue sites increases a difficulty in selecting a focal depth of the Raman spectrometer that will optimize a resolution of the Raman signal.

Systems and methods disclosed herein address one or more of these or other challenges by utilizing data associated with one or more sensors to calibrate or improve an accuracy of one or more other sensors. For example, a value for path length can be obtained from skin geometry data, which can improve a pulse oximetry sensor such as a near infrared (NIR), reflectance, or transmittance sensor. As another example, the present disclosure addresses various challenges related to leveraging the Raman scattering signatures for prediction of glucose by harmonizing data from a plurality of non-invasive physiological sensors. For instance, a focal depth of the Raman spectrometer can be selected based on tissue geometry data, which can improve the Raman spectrometer, and possibly increase an accuracy of a blood glucose measurement. Similarly, using data from one or more sensor, the Raman signal can be isolated by reducing or removing an effect of Fluorescence on a collected signal, or removing an effect of attenuation of the signal due to absorption.

System Overview

FIG. 1 illustrates an example patient monitoring system 100 that includes a patient monitor 102, a first sensor 104A, and a second sensor 104B. In addition, the patient monitoring system 100 can include one or more other sensors 104N. Sensors 104A, 104B, and 104N can interrogate tissue sites 106A, 106B, and 106N, respectively, of a patient. In some cases, tissue sites 106A, 106B, and 106N can be the same or substantially proximate tissue sites, while in other cases one or more of the tissue sites 106A, 106B, or 106N can be different. Sensor data from the sensors 104A, 104B, or 104N can be utilized to determine one or more physiological parameters or patient vitals. For example, the patient monitor 102 can receive a signal from the one or more of the sensors 104A, 104B, or 104N and can determine, based on the received signal(s), one or more physiological parameters or one or more measurements that can be used to determine a physiological parameter.

The sensors 104A, 104B, and 104N can each be the same type of sensors, or one or more of the sensors 104A, 104B, and 104N can be different from each other. For example, the sensors 104A, 104B, and 104N can include, but are not limited to, any combination of an optical coherence tomography (OCT) device, a spectrometer (for example, a Raman spectrometer), a plethysmograph sensor such as a pulse oximetry device (for example, a near infrared (NIR), reflectance and/or transmittance device), a pressure sensor, an electrocardiogram sensor, a bioimpedance sensor, or acoustic sensor, among other sensors.

Two or more of the sensors 104A, 104B, or 104N can be configured to interrogate the same tissue site. For example, two or more of the senor sensors 104A, 104B, or 104N can be positioned proximate each other such that they can interrogate the same tissue, such as a finger, a thumb, a thenar space, a hand, a wrist, a forearm, a nose, a limb, a head, an ear, a neck, an upper body, or a lower body. In addition or alternatively, two or more of the sensors 104A, 104B, or 104N can be configured to interrogate different tissue sites.

In some cases, one or more of the sensors 104A, 104B, or 104N can be integrated into an apparatus, such as an apparatus that is wearable by a user. For example, one or more of the sensors 104A, 104B, or 104N can be integrated into a glove that when worn by a user allows the sensor(s) to interrogate one or more tissue sites. Similarly, one or more of the sensors 104A, 104B, or 104N can be incorporated in or attached to various other apparatuses, including, but not limited to, a sock, a shirt, a sleeve, a cuff, a bracelet, a glove, or the like.

In some cases, data from a single sensor 104A, 104B, or 104N does not provide enough reliable information to determine certain physiological parameters. For example, a number of factors can affect an accuracy of sensor data including, but not limited to, patient movement, sensor placement, interference, the type of sensor being used, the expansion and contraction of the patient's vascular system, assumptions made during calculations, skin temperature, pressure, or the like. In addition or alternatively, the determination of some physiological parameters (for example, glucose concentration) may require more information than a single sensor can provide.

To solve this and other problems, the patient monitor 102 (or one or more of the sensors) can harmonize or compare data from two or more sensors, which can allow for a determination of more accurate or reliable data, or can allow for a determination of one or more additional physiological parameters, such as blood glucose concentration.

As one example, the patient monitor 102 receives a first signal from a first sensor 104A, the first signal corresponding to an interrogation of the first tissue site 106A by the first sensor 104A. Further, the patient monitor 102 receives a second signal from a second sensor 104B, the second signal corresponding to an interrogation of the second tissue site 106B by the second sensor 104B. Based on the first signal, the patient monitor 102 can make adjustments to modify the second sensor or the second measurement to improve the accuracy or reliability of the second sensor or the second measurement. For instance, adjustments can include, but are not limited to, adjusting an intensity, power, position, or timing of the second sensor 104b or adjusting values corresponding to the measurement of the second physiological parameter. For example, the patient monitor 102 can modify the second measurement or calculations for a physiological parameter (for example, introduce an offset, adjust assumed or estimated values, filter a signal, etc.) to account for information from the first sensor. In addition or alternatively, the patient monitor can adjust a confidence value associated with the first, second, or another measurement.

As described above, based at least in part on the first and second signals, the patient monitor 102 can determine a physiological parameter. The physiological parameter can be a value which may not be independently determinable from data from either of the first sensor or the second sensor alone. For example, data from the first sensor can be utilized to determine a path length, data from the second sensor can be utilized to determine an absorbance, and the physiological parameter can include a concentration of an analyte, such as glucose. As another example, data from the first sensor can be utilized to determine a path length or absorbance, the second sensor can correspond to a Raman spectrometer, and the physiological parameter can include a concentration of an analyte, such as glucose.

The patient monitor 102 can include a digital signal processor (DSP) that receives the signals generated by the one or more sensors 104A, 104B, or 104N (for example, through a front-end unit) and determines parameters, for example, those indicative of the physiological condition of the patient, using the received signals. The patient monitor 102 can, for example, determine physiological parameters corresponding to the patient, such as an amount of light absorbed, transmitted through, or reflected at a tissue site, path length (for example, distance that light travels through the material), concentration of an analyte, bioimpedance, tissue dielectric constant, pulse rate (PR), pulse pressure variation (PPV), pleth variability index (PVI®), stroke volume (SV), stroke volume variation (SVV), peripheral capillary oxygen saturation ($SpO_2$), mean arterial pressure (MAP), central venous pressure (CVP), pulse pressure (PP), perfusion index (PI), total hemoglobin (SpHb®), carboxyhemoglobin (SpCO®), methemoglobin (SpMet®), oxygen content (SpOC®), or acoustic respiration rate (RRa®), among other parameters. In some aspects, the patient monitor 102 can derive or use one or more relationships (for instance, a set of linear equations) from two or more of the determined parameters. The patient monitor 102 can utilize the one or more relationships to determine the patient's glucose levels, systemic vascular resistance (SVR), CO, or arterial blood pressure (BP), among other parameters.

The patient monitor 102 can further compare or analyze one or more of the determined parameters (for instance, at least two of the determined parameters or one determined parameter and a previous or model parameter) to adjust how a parameter is measured or calculated to make the measured parameter more accurate or reliable, to adjust a sensor to make the measured parameter more accurate or reliable, to calculate, derive or determine an accuracy or a confidence value of a measured parameter, to isolate a parameter, or to determine another parameter based on the one or more parameters. The sensors, in addition to or alternatively than the patient monitor, can coordinate with each other to coordinate data or adjust calculations to enhance an accuracy or reliability of measurements. In addition or alternatively, the patient monitor 102 can use the data to increase an accuracy of one or more calculations, calculate a previously unknown or estimated physiological parameter, calibrate data, or compensate for various circumstances that might otherwise result in inaccurate or unreliable data.

Additional Implementations

The patient monitor 102 can be connected to one or more (for instance, three, four, five, or six) sensors, such as the sensors 104A, 104B, or 104N, that are detecting from a patient and use the signals received from the sensors to determine one or more physiological parameters including, but not limited to, glucose, $SpO_2$, PPR, PVI® (for instance, via a palm, thumb or finger plethysmography sensor), SV, MAP, CVP, PP, or PI (for instance, via a palm, thumb or finger plethysmography sensor), among other parameters such as those described herein.

Moreover, the patient monitor 102 can utilize any of the techniques described herein to determine whether any measurement described herein (using any of the sensors described herein) is valid. The patient monitor 102 can be configured to show (for example, on a display) information about a valid or invalid measurement, activate an indicator light (such as an LED), trigger an alarm, adjust one or more sensors or parameters (for instance, based on a received sensor signal), or display any data.

The patient monitor 102 can wirelessly or using wires receive, via an input of the patient monitor 102, a signal from one of the sensors 104A, 104B, or 104N. The received signal may take various forms, such as a voltage, a current, or charge. An operational amplifier (op-amp) of the patient monitor 102 can increase the amplitude, as well as transform the signal, such as from a current to a voltage. An anti-aliasing filter (AAF) of the patient monitor 102 can then process of the output signal from the op-amp to restrict a bandwidth of the output signal from the op-amp to approximately or completely satisfy the sampling theorem over a band of interest. An analog-to-digital convertor (ADC) of the patient monitor 102 can convert the output signal from the AAF from analog to digital. The output signal from the ADC can then be sampled by a first processor of the patient monitor 102 at a relatively high speed. The result of the sampling can next be downsampled by a second processor of the patient monitor 102, which may be the same or different from the first processor, before waveform analysis may be performed by a DSP.

Figure 2:
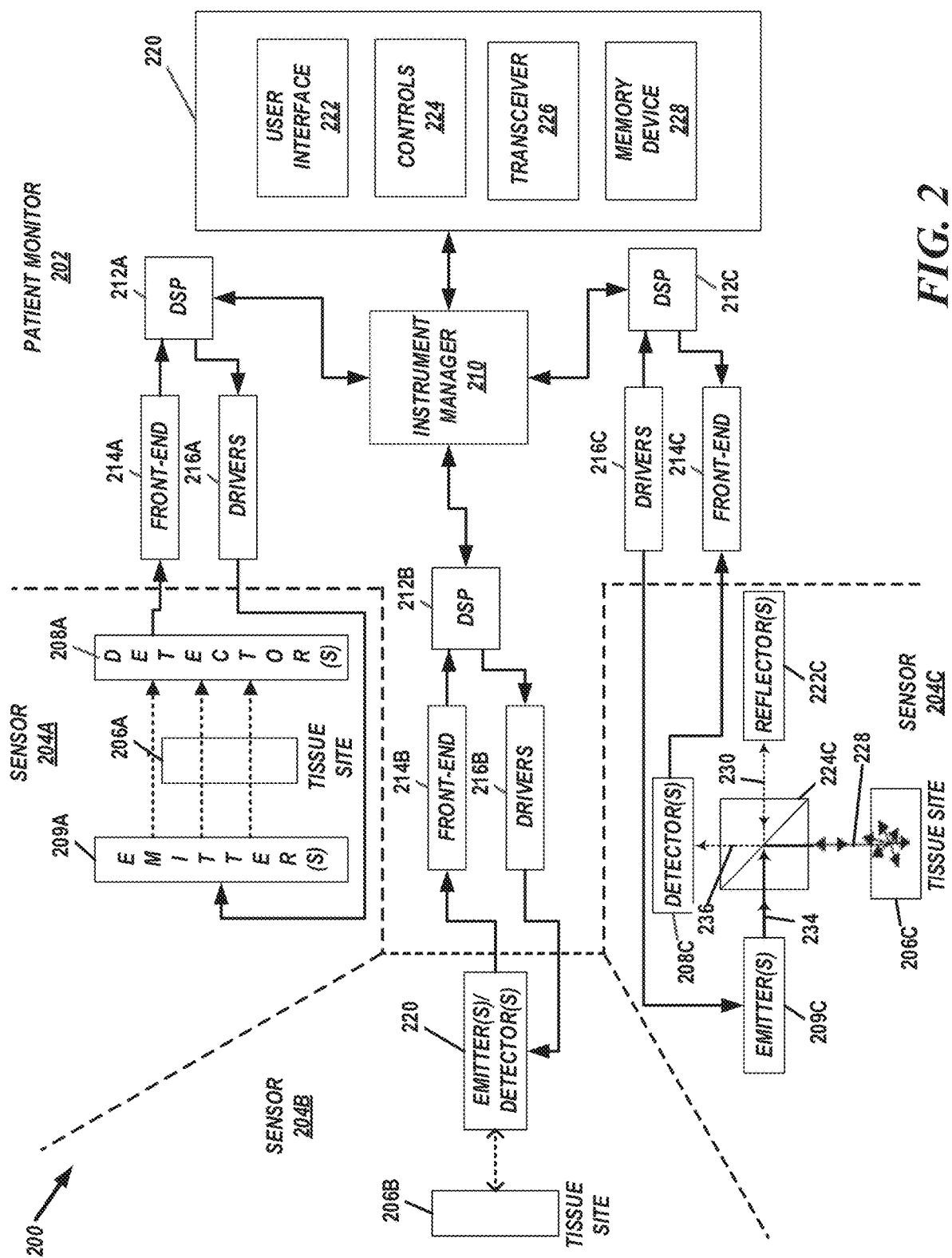
FIG. 2 illustrates a block diagram of an example patient monitoring system.

FIG. 2 illustrates a block diagram of an example patient monitoring system 200, which can be an embodiment of the patient monitoring system 100. The patient monitoring system 200 can include a patient monitor 202, a first non-invasive physiological sensor 204A, a second non-invasive physiological sensor 204B, or a third non-invasive physiological sensor 204C. Furthermore, it should be noted that fewer, additional, or different sensors may be included in patient monitoring system 200.

The sensors 204A, 204B, or 204C can respectively detect from tissue sites 206A, 206B, and 206C of a patient. Each of the sensor can measure from the same or a similar tissue site. For example, sensor 204A can take a measurement and sensor 204B can take a subsequent measurement on the same tissue or at the same location. This may allow the system to more easily harmonize the data from the sensors or use data from one sensor to improve data or calculation based on another sensor. The tissue sites 206A, 206B, and 206C can be different. As a non-limiting example, tissue site 206A can include a thenar space of a patient's hand, and tissue sites 206B, 206C include a thumb of the patient, such as a base of the thumb. It should be noted, however, that fewer, more or different sensors can be include in system 200.

The DSP 212A can communicate via drivers 216A with the plethysmography sensor 204A and receive via a front-end 214A one or more light intensity signals indicative of one or more physiological parameters of the patient or one or more measurements that can be used to determine one or more physiological parameters. For example, a signal can be indicative of an intensity of light reflected, refracted, scattered, absorbed, or transmitted at a tissue site. The drivers 216A can convert digital control signals into analog drive signals capable of driving emitters 209A to illuminate the tissue site 206A. For example, the light emitted by emitters 209A can have an infrared (IR), near infrared (NIR), red, ultra-violet (UV), visible, or other wavelength. The detector(s) 208A can, in turn, generate one or more composite analog light intensity signals responsive to light detected by the detector(s) 208A after attenuation, reflection, refraction, scattering, absorption, etc. at the tissue site 206A. The emitter(s) 209A or detector(s) 208A include a fiber-optic component for illumination and collection, respectively. For example, the emitter(s) 209A can be positioned on a tissue site 206A (for example, on top, on the bottom, on the side, etc.) and the detector(s) 208A can be positioned on an opposite portion of the tissue site 206A.

The front-end 214A can convert the one or more composite analog light intensity signals from the detector(s) 208A into digital data and input the digital data into the DSP 212A. The digital data from the front-end 216A can correspond to at least one of a plurality of physiological parameters as described herein. For example, the digital data from the front-end 216A can be representative of a change in the absorption of particular wavelengths of light as a function of the changes in the tissue site 206A resulting from pulsing blood.

The DSP 212A can include one or more data or signal processors configured to execute one or more programs for determining physiological parameters from input data. The DSP 212A can perform operations that include calculating or outputting one or more physiological measures, such as absorbance, path length, PVI® and other parameters described herein. The operations performed by the DSP 212A can be implemented in software, firmware or other form of code or instructions, or logic or other hardware, or a combination of the above.

The instrument manager 210 can communicate with one or more input or output devices 220. The one or more input or output devices 220 can include a user interface 222, controls 224, a transceiver 226, and a memory device 228.

The user interface 222 can include a numerical or graphical display that provides readouts of measures or parameters, trends and bar graphs of measures or parameters, visual indications of measures or parameters, visual indicators like LEDs of various colors that signify measurement magnitude, or device management interfaces, which can be generated by LEDs, LCDs, or CRTs, for example. The user interface 222 can include an audible output device that provides readouts or audible indications of measures or parameters. The user interface 222 can include one or more input devices like a keypad, touch screen, pointing device, voice recognition device, and computer that can be used to supply control or configuration data, such as initialization settings, from the user interface 222 to the instrument manager 210. In some implementations, the user interface 222 can be an interface for devices as well as users.

The controls 224 can be outputs to medical equipment, such as drug administration devices, ventilators, or fluid IVs, so as to control the amount of administered drugs, ventilator settings, or the amount of infused fluids. The patient monitor 202 can use the controls 224 to automatically treat the patient (for instance, provide fluid to the patient, provide medication to the patient, turn on a fan to cool the patient, or adjust a temperature of a room to heat or cool the patient) in response to determining that the patient may benefit from treatment.

The transceiver 226 via an antenna can transmit information about operation of the patient monitor 202 to an electronic device or receive control or configuration data for operating the patient monitor 202. The transceiver can, for example, communicate via a computer network or intermediary device or directly with the electronic device using electromagnetic radiation.

The memory device 228 can be used to store information about operation of the patient monitor 202. This information can, for example, include readouts of measures or parameters, trends and bar graphs of measures or parameters, visual indications or indicators.

The DSP 212B can receive via a front-end 214B one or more light intensity signals indicative of one or more physiological parameters of the patient. The drivers 216B can convert digital control signals into analog drive signals capable of driving emitters/detectors 220 to illuminate the tissue site 206B. For example, the light emitted by emitters/detectors 220 can be infrared (IR), near infrared (NIR), red, ultra-violet (UV), visible, or other wavelength. The emitters/detectors 220 can, in turn, generate one or more composite analog light intensity signals responsive to light detected by the emitters/detectors 220 light is reflected, refracted, scattered, absorbed, or attenuated at a tissue site 206B. The emitters/detectors 220 include a fiber-optic bundle that has illumination and detection fibers. In addition, for example, as described with respect to FIG. 1, the emitters/detectors 220 can be separate.

The front-end 214B can convert the one or more composite analog light intensity signals from the emitters/detectors 220 into digital data and input the digital data into the DSP 212B. The digital data from the front-end 214B can correspond to at least one of a plurality of physiological parameters, as described herein. The digital data from the front-end 214B can be representative of a change in the absorption/reflection of particular wavelengths of light as a function of the changes in the tissue site 206B resulting from pulsing blood.

The DSP 212B can include one or more data or signal processors configured to execute one or more programs for determining physiological parameters from input data. The operations performed by the DSP 212B can be implemented in software, firmware or other form of code or instructions, or logic or other hardware, or a combination of the above.

Sensor 204C includes a detector 208C, a light source 209C, a beam splitter 224C, and a reflector 222C. The light source 209C can emit light having an approximately equal wavelength, a spectrum of wavelengths, or a few different wavelengths, for example, two. For example, the wavelengths can be selected based on the absorption spectrum.

As illustrated, light beams from the light source 209C are split using the beam splitter 224C into reference arm light beams 230 and sample arm light beams 228. After the light beams 234 are split, the reference arm light beams 230 travel down the reference arm to interact with the reflector 222C, and the sample arm light beams 228 travel down the sample arm to interact with the tissue 206C, for example, from the base of a patient's thumb.

The tissue site 206C can absorb, reflect, scatter, or refract the sample arm light beams 228. Some of the sample arm light beams 228 are reflected back to the beam splitter 224C. The beam splitter 224C can direct at least some of the reflected sample arm light beams 228 to the detector 208C.

The light beams traveling down the reference arm interact with a reflector 222C and are reflected back to the beam splitter 224C. Similar to the reflected sample arm light beams 228, the reflected reference arm light beams 230 are also directed to the detector 208C by the beam splitter 224C. Reflected signals from the sample arm and reference arm and are presented to photodetector 208C for measurement.

The tissue volume with which the light interacts (referred to as the interaction volume) can be determined by the spot size of the imaging optics (surface area) and the coherence length of the light (depth). Thus, the reference arm can determine the depth within the interaction volume from which scattered light is measured. The patient monitor 200 uses the detected signals obtained from the interference of the reflected sample arm light beams 228 and the reflected reference arm light beams 230 to calculate tissue geometry data, such as a skin geometry of one or more skin layers.

Although not illustrated in FIG. 2, imaging optics can also be used to focus the sample arm light beams 228 prior to interacting with the tissue site 206C. Furthermore, the end of the sample arm and imaging optics can be placed in close proximity to the tissue site 206C. The reference arm and reflector 222 are configured such that appropriate wavelength and polarization selected such that the appropriate depth of the tissue is measured.

The DSP 212C can receive via a front-end 214C one or more signals indicative of one or more physiological parameters of the patient, such as path length. The drivers 216C can convert digital control signals into analog drive signals capable of driving emitters 209C to illuminate the tissue site 206C. The detectors 208C can, in turn, generate one or more composite analog signals responsive to light detected by the detectors 208C.

The front-end 214C can convert the one or more composite analog signals from the detectors 208C into digital data and input the digital data into the DSP 212C. The digital data from the front-end 216C can correspond to at least one of a plurality of physiological parameters, as described herein. The DSP 212C can include one or more data or signal processors configured to execute one or more programs for determining physiological parameters from input data. The operations performed by the DSP 212C can be implemented in software, firmware or other form of code or instructions, or logic or other hardware, or a combination of the above.

One or more of the components relating to signal acquisition or processing (for example, front end 214A, 214B, 214C, drivers 216A, 216B, 216C, DSP 212A, 212B, 212C, etc.) can be incorporated into one or more connecting cables, the sensors themselves, or are otherwise closer to the sensor sites. As such, the patient monitor 202 can include primarily the input or output devices 220 and the instrument manager 210, (if appropriate). In addition, some of the components are illustrated as separate units but can be combined. For instance, front end 214A, 214B, 214C can be combined into one or more front ends, drivers 216A, 216B, 216C, can be combined into one or more drives, DSP 212A, 212B, 212C can be combined into one or more DSPs, etc. By reducing the number of components included in the patient monitor 102, 202, the monitor can be smaller in size or more portable, which can be more convenient for home or "spot check" use.

Although not illustrated in FIG. 1 or 2 patient monitors 102, 202, or cables connecting the patient monitors to the sensors can further include one or more outputs that supply the signal(s) from one or more of the sensors to one or more other electronic devices for further processing. As one example, the signal(s) from one or more of the sensors can be output in parallel by one or more of the sensors or the cables that couple the one or more sensors to the patient monitor 102, 202. In another example, the patient monitors 102, 202 can include one or more outputs for outputting copy(ies) of the signal(s) from one or more of the sensors. The copy(ies) of the signal(s) can also be adjusted relative to the original(s) with filtering, scaling, or other changing prior to being provided to the one or more other electric devices.

Optical Coherence Tomography

Optical coherence tomography, or OCT, is an optical imaging technique using light waves that produces high-resolution imagery of biological tissue. OCT creates its images by focusing a beam of light into a medium and interferometrically scanning the depth of a linear succession of spots and measuring the absorption and/or the scattering of the light at different depths in each successive spot. In some cases, the data can be processed to present an image of the linear cross section of the medium scanned.

A light source can output a beam of light having a broad spectrum of wavelengths. The beam of light can be collimated and pass a beam splitter such that a portion of the beam of light is directed towards the tissue and a portion of the beam of light is directed toward a reference arm. The light can be either polarized or non-polarized. A polarizer located on one edge of the beam splitter can polarize the light linearly, elliptically, or circularly, as desired. The path length of the reference arm can be changed based on the desired measurement depth into the tissue. The wavelength can be centered at, for example, 1310 nm with a 50 nm bandwidth. In other cases, the wavelength can be 1060 nm with a 70 nm bandwidth. The light source can be selected to have a center wavelength anywhere between 400 nm and 1700 nm with a bandwidth of up to 150 nm. It is understood that different light sources with different bandwidths can be chosen to optimize penetration depth into the tissue and optimize the depth resolution of sensitivity to skin structures. The reflected light from the tissue can be collected using a converging lens and be directed back through the beam splitter to a photodetector where it is recombined with a portion of the reference arm beam to form an interference pattern. A processor can use the signals from the photodetector to render an image of the tissue.

OCT can provide a non-invasive method for identifying one or more characteristics of a tissue's structure. For example, OCT data (which can be referred to as tissue geometry data) can include an indication of a boundary between the main skin layers, such as the epidermis (outermost layer of the skin), the dermis (layer beneath the epidermis), or the hypodermis (layer directly below the dermis and serves to connect the skin to the underlying fibrous tissue of the bones or muscles). The epidermis is further divided into five, separate layers (Stratum Corneum, Stratum Lucidum, Stratum Granulosum, Stratum Spinosum, and Stratum Basale) and the dermis is divided into two, separate layers (the papillary dermis and the reticular dermis). In some cases, OCT data can provide an indication of a boundary between any of these layers. In addition or alternatively, OCT data can include can include an indication of a thickness of any of the epidermis, dermis, or hypodermis, or their individual layers.

Figures 3A, 3B:
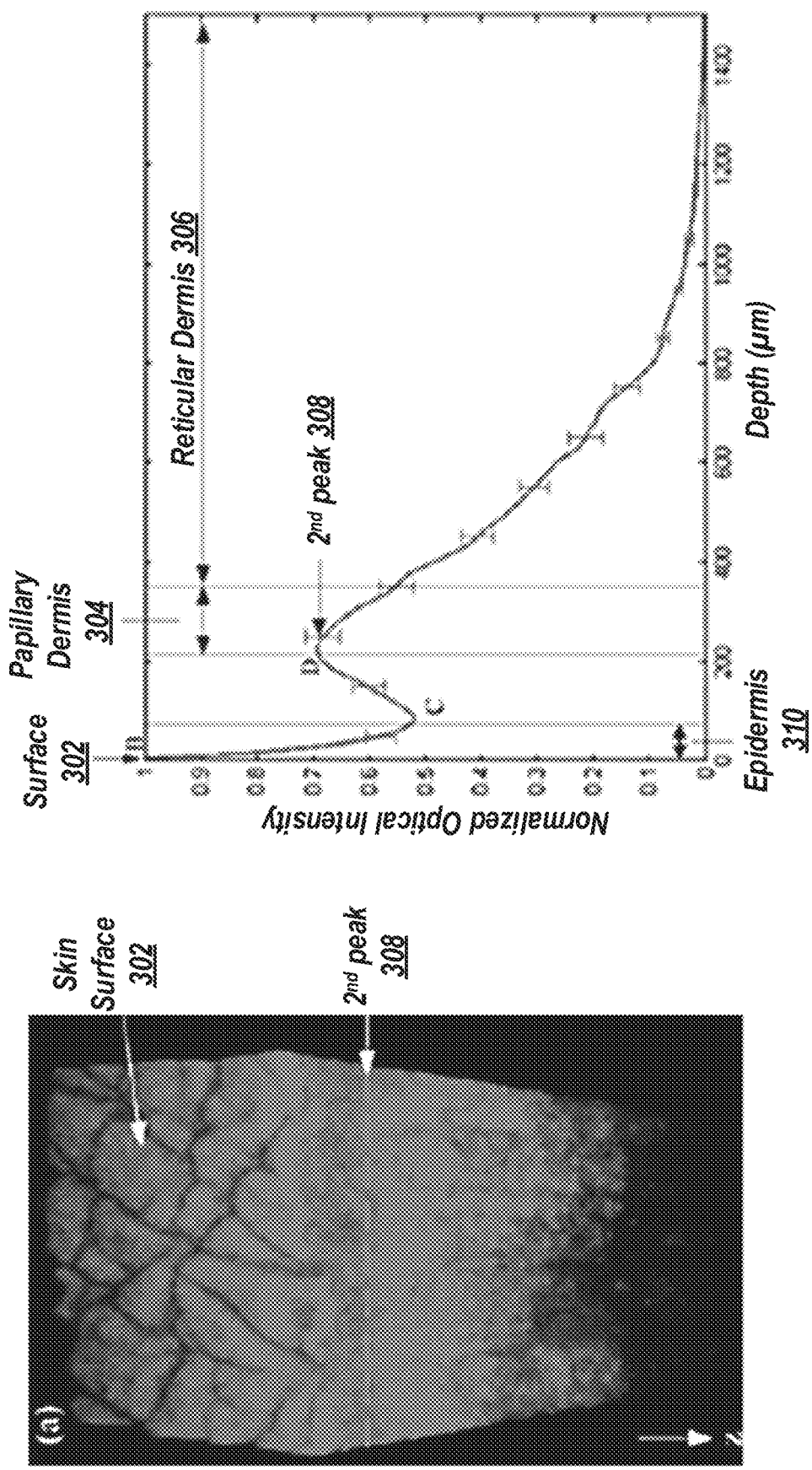
FIG. 3A illustrates an example 3D OCT image obtained from a volar side of forearm skin.
FIG. 3B illustrates an example one-dimensional distribution of light intensity versus depth graph obtained by averaging scans of the image of FIG. 3A.

For example, FIG. 3A illustrates an example 3D OCT image obtained from a volar side of forearm skin, and FIG. 3B illustrates an example one-dimensional distribution of light intensity vs. depth obtained by averaging Amplitude scans (A-scans) in the reconstructed OCT 3D image of FIG. 3A. The slope of the line of FIG. 3B is indicative of index of refraction of tissue. A difference in the index of refraction, or a difference in slope, can indicate a new skin or tissue layer because each layer may have a different index of refraction. As illustrated, the first peak 302 corresponds to the skin surface 302, and the second peak 308 corresponds to the dermoepidermal junction, which is the area of tissue that joins the epidermis 310 and the dermis layers (for example, the papillary dermis 304) of the skin. Accordingly, using OCT data, the system 200 can determine a thickness of one or more of various skin layers such as, but not limited to, the epidermis 310, the dermoepidermal junction, the papillary dermis 304, the reticular dermis 306, or the like.

In some cases, OCT data can provide an indication that an OCT sensor is interrogating an unfavorable tissue site. An unfavorable tissue site can include any tissue site that might provide distorted or inaccurate OCT data (relative to desired OCT data), such as tissue sites that include at least a portion of a hair follicle, a pore, a bone, a finger- or toe-nail, a pimple, a mole, a scar, a blister, a callous, debris, other skin imperfection, or the like.

A particular tissue site can retain its specific optical profile over time, and that optical profile can be different from another tissue site. Accordingly, to maintain data harmonization capabilities, it can be advantageous for sensors to interrogate the same or a substantially proximate tissue site. One problem associated with interrogating the same or a substantially proximate tissue site relates to the subsequent placement of a sensor after it has been removed from the patient or when it is shifted in some way from its original positioning. For example, a subsequent OCT measurement or set of measurements can occur minutes, hours, days, weeks, or some other period of time after the first measurement, and it can be unreasonable to require a patient to wear or interact with the OCT sensor for the duration of that period of time. Nonetheless, even though the OCT sensor has been separated from the patient or shifted from its original position, it can be advantageous for the subsequent OCT measurement(s) to occur at the same location as the first measurement. For example, as described herein, a first tissue site may have a different tissue structure, density, depth, hydration, analyte concentration, or the like than a second, different tissue site. Thus, if the OCT sensor is placed at the same location for each measurement, then previous calculations, determinations, or the like can be utilized, which can simplify any calibrations or corrections to sensor data, among other things.

To solve these and other problems, tissue geometry information associated with OCT data can be utilized to determine whether a subsequent placement of the OCT sensor allows the OCT sensor to interrogate the tissue site corresponding to the tissue site of the first OCT measurement(s). For example, a processor can compare the first tissue geometry data associated with the first OCT measurement(s) with the subsequent tissue geometry data associated with the subsequent OCT measurement(s). If the subsequent tissue geometry data does not correspond to the first tissue geometry data, then the processor can cause one or more actions to occur. For example, the processor can cause an output to indicate that the subsequent tissue geometry data does not correspond to the first tissue geometry data. In other words, the processor can cause an output to indicate that the subsequent placement of the OCT sensor is incorrect, or is different from the first OCT sensor placement, or the processor can cause an output to indicate a probe-off condition. In addition or alternatively, the processor can cause the OCT sensor to be re-positioned. For example, based on the comparison, the processor can suggest a new placement of the OCT sensor, which may more closely correspond to the first placement of the OCT sensor. In addition or alternatively, the processor can control a motorized component to re-position to the OCT sensor such that it more closely corresponds to the first placement of the OCT sensor. Still, in some implementations, the processor can calibrate other sensors based on the subsequent tissue geometry data, rather than the first tissue geometry data.

Alternatively, if the subsequent tissue geometry data does correspond to the first tissue geometry data, then the processor can cause one or more other actions to occur. For example, the processor can cause an output to indicate that the subsequent tissue geometry data does correspond to the first tissue geometry data. In other words, the processor can cause an output to indicate that the subsequent placement of the OCT sensor is correct, as compared to the first placement of the OCT sensor. In addition or alternatively, the processor can calibrate other sensors based on the first tissue geometry data or the subsequent tissue geometry data.

Bioelectrical Impedance (Bioimpedance)

Impedance can be characterized as a physical variable describing the resistance characteristics acting on an electric current. Bioelectrical impedance is based on the principle that tissues or fluids of a patient have different impedances, that is, opposition to the flow of the electric current, which in turn may be dependent on variables such as water and electrolyte content, to name a few. Using a bioelectrical impedance, analysis can be performed to examine electrical, capacitive, or resistive characteristics of tissue to provide information on a noninvasive basis.

Mathematically, bioelectrical impedance can be represented as a complex number including a real component (resistance) and an imaginary dimension (reactance). For example, the bioelectrical impedance can be calculated using the following equation below:

$$Z = R + jX = |Z|e^{j\theta} \quad \text{(Equation 2)}$$

where R is resistance, X is reactance, |Z| is amplitude, and $\theta$ is phase.

A number of physiological characteristics or parameters can be calculated or estimated using determined bioelectrical impedance characteristics, such as water content, body cell mass (BCM), extra cellular mass (ECM), extracellular fluid (ECF), extracellular water (ECW), fat-free mass (FFM), fat mass (FM), total body water (TBW), electrolyte composition, cell membrane mass, cell membrane function and the like.

Biological tissues can have complex electrical impedance which is dependent, for instance, on the frequency of the electrical applied field or tissue cellular structure. Therefore, the electrical impedance of tissue is a function of its structure and it can be used to differentiate or determine characteristics of one or more layers to tissue.

The system can include a bioimpedance sensor configured to apply an electrical signal to the tissue, which can include one or more of various voltages, currents, frequencies (for example, 1 kHz to 2.5 GHz), or fields. In some cases, the path length of the signal can vary based on the applied electrical signal. For example, low frequency signals may primarily reflect the extracellular environment, while high frequency signals may reflect both the intra- and extracellular environment. In addition, the bioimpedance sensor can be configured to measure characteristics of the applied electrical signal as it passes (or after it has passed) through tissue. For example, the bioimpedance sensor can measure a voltage, current, frequency, magnetic field, etc., which can be indicative of a voltage difference across tissue or a biological impedance of a tissue, to name a few.

Figure 4:
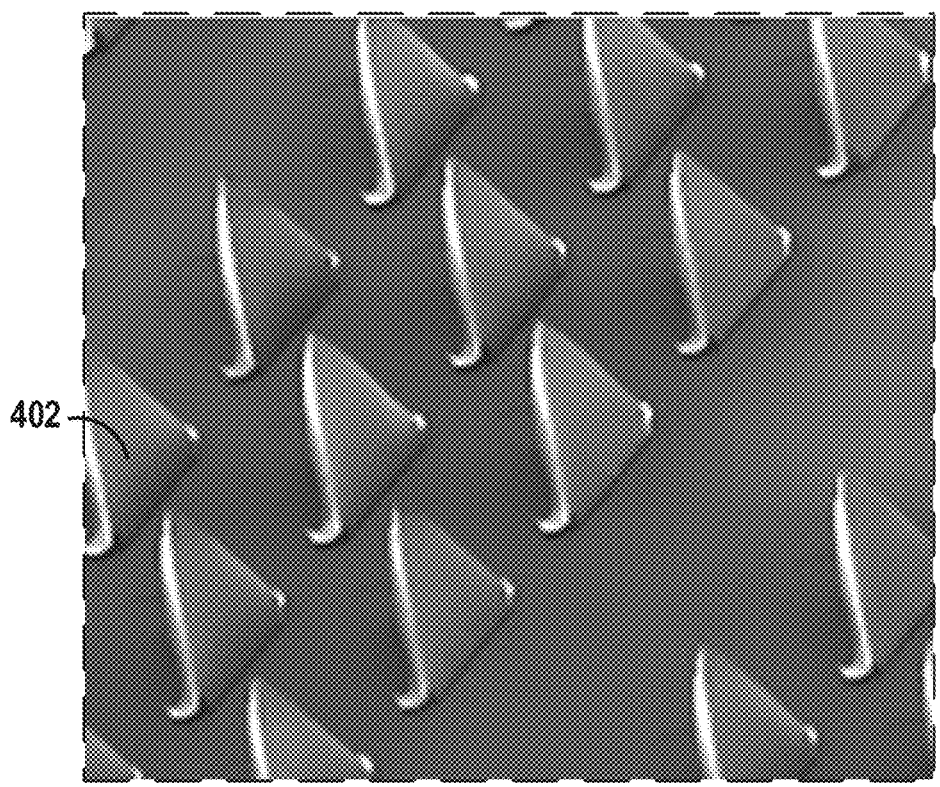
FIG. 4 illustrates example micro-invasive elements of a bioimpedance sensor.

One or more properties of skin may disturb or disrupt bioimpedance measurements. For example, the stratum corneum can limit bioimpedance measurements. Accordingly, as illustrated in FIG. 4, the bioimpedance sensor can include a micro-invasive element 402 that is configured to penetrate the stratum corneum layer. For example, the bioimpedance sensor can include spikes or other elements that penetrate approximately 10-20 μm deep.

Figure 5:
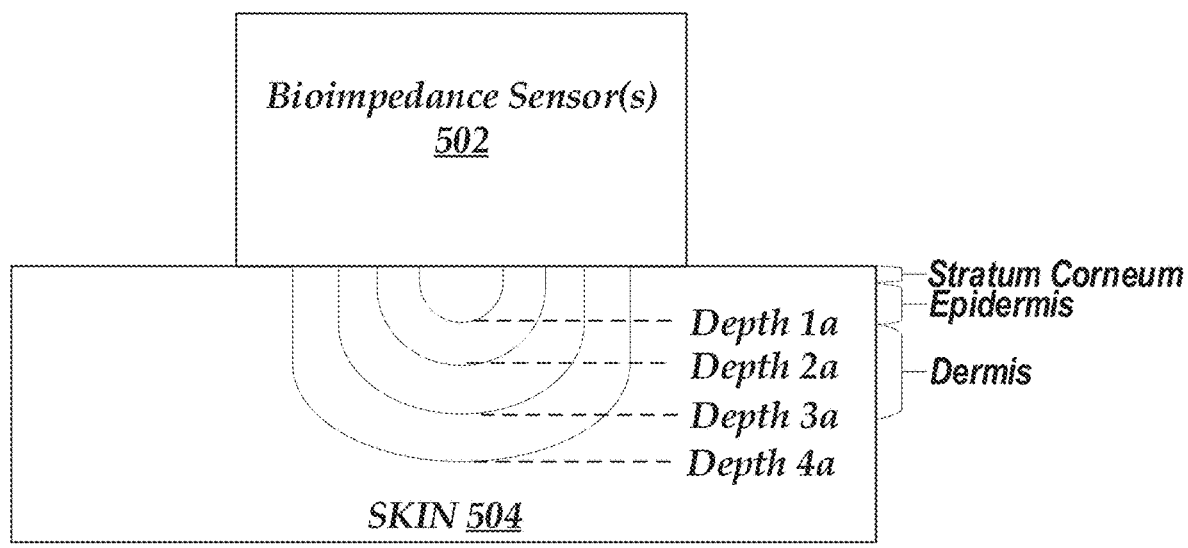
FIG. 5 illustrates an example bioimpedance sensor.

FIG. 5 illustrates an example bioimpedance sensor 502. The sensor 502 can include multiple channels of spiked regions configured to penetrate the skin. As shown, spacing between the channels can allow for shallow and deep penetration, such that the bioimpedance sensor 502 can measure impedance at various depths, such as Depths 1a, 2a, 2b, 3a, or 4a.

Using information from the bioelectric sensor(s) 502, the system 200 can determine information about the tissue geometry. For example, based on bioelectric sensor data, the system can determine a cellular structure of the tissue, which may affect various physiological parameters, such as path length or absorption. In addition, based on bioelectric sensor data, the system can determine information related to hydration of the skin or tissue. For example, water content can be directly related to skin thickness. As described herein, in some cases, the system can select a focal depth of the Raman spectrometer based at least in part on tissue geometry data.

Tissue Dielectric Constant

In addition or alternatively to bioimpedance or OCT, the system can utilize one or more tissue dielectric constant sensors to determine various tissue geometries or tissue information, including, but not limited to a dielectric constant of tissue. For example, the system 200 can include a plurality of probes for different measuring depths, such as 0.5 mm, 1.5 mm, 2.5 mm, and 5 mm effective depths, and the system can determine a dielectric value at each of the different depths. In addition or alternatively, the system 200 can include one or more probes that are each configured to measure at different depths, such as 0.5 mm, 1.5 mm, 2.5 mm, and 5 mm effective depths, and the system can determine a dielectric value at each of the different depths. The dielectric value can correlate with water content, which can be tied to tissue structure.

Accordingly, the tissue dielectric constant can provide information which can be combined with other sensor information (for example, OCT, bioimpedance, reflectance or transmission measurements, Raman measurements) to determine more accurate physiological measurements, such as blood glucose levels. For example, the bioimpedance or tissue dielectric constant data can provide information that correlates with local tissue hydration, or can provide information about different skin layers or cellular structure information. Furthermore, bioimpedance or tissue dielectric constant sensors can provide real-time measurements that can provide information about physiological "noise" within the tissue, which can be used to calibrate other measurements or calculations. As described herein, in some cases, the system can select a focal depth of the Raman spectrometer based at least in part on tissue geometry data.

Raman Spectroscopy

The Raman effect is a light-scattering phenomenon that can provide insight as to one or more characteristics of an analyte in a sample. When light irradiates a tissue, a fraction of the light is scattered, meaning it emerges in directions other than that of the incident (incoming) beam. Most of this scattered light, generally referred to as Rayleigh scattering, emerges at the original frequency ($f_0$) and wavelength of the incident beam. A small portion of the scattered light, however, emerges at some shifted frequency ($f_s$) that is different from, and usually lower than, the original frequency ($f_0$) and has wavelengths different from that of the incident light. The process leading to this small portion of the scattered light is termed the Raman effect or Raman scattering.

Raman scattering can occur with a change in vibrational or rotational energy of a molecule. Accordingly, the Raman spectra can contain information about the specific chemical substance in the irradiated tissue. For example, Raman scattering yields a set of characteristic peaks in a spectrum, which is a "fingerprint" of a specific chemical substance. Therefore, Raman has high specificity in glucose measurements.

Raman spectroscopy has exhibited promise with respect to blood glucose detection, for example, due to its capability to gain information about the molecular constitution non-invasively. For example, features (such as peaks) of the Raman spectra are considered the Raman "fingerprints" of analytes, such as glucose. Accordingly, using an isolated or semi-isolated Raman signal, the system can identify physiological data, such as information regarding a patient's blood glucose level. However, for various reasons, it has been challenging to isolate a pure Raman signal from a signal obtained from a Raman spectrometer.

The signal collected through Raman spectroscopy is based at least in part on the collection optics and the focal distance/depth of the optics into the tissue. In some cases, the system can use data from one or more sensors to select an appropriate focal depth. For example, a focal depth can be selected that may provide a high or the highest resolution of the Raman or collected signal. In addition or alternatively, a focal depth can be selected that will allow the Raman spectrometer to focus on a particular location of the tissue, such as the capillary beds. For example, OCT, bioelectrical impedance, or tissue dielectric constant measurements may provide tissue geometry data (for example, structural and functional information) that can be used to select a focal depth into the tissue. For example, the selection can be based at least in part on a water content of a portion of the tissue, a thickness of one or more skin layers, or a particular location of tissue, such as the capillary beds.

Although complex, an approximation of a measurement obtained from a Raman spectrometer can be determined using one or more of the following equations:

$$I_1 = I_0 e^{-A_1} \quad \text{(Equation 3)}$$

$$R_0 = R_A I_1 \quad \text{(Equation 4)}$$

$$F_0 = \Phi I_1 \quad \text{(Equation 5)}$$

$$I_2 = \Sigma((R_0 + F_0) e^{-A_2}) \quad \text{(Equation 6)}$$

where $I_0$ is an intensity of excitation light, $I_1$ is an intensity of scattered light, $A_1$ is a first interrogation volume, $R_A$ represents Raman activity, $R_0$ is an intensity Raman scattering at a specific wavelength of light, $F_0$ is an intensity of Florescence at the specific wavelength of light, $\Phi$ represents quantum efficiency, $A_2$ represents a second interrogation volume, and $I_2$ is an intensity of measured light. From these relationships, it can be seen that the intensity of measured light ($I_2$) is dependent on the intensity of Raman scattering ($R_0$), the intensity of Fluorescence ($F_0$), or the second interrogation volume ($A_2$), among other things. Due to the nature of the Raman spectroscopy, the intensity of Raman scattering ($R_0$) is often of very low intensity. In various aspects, the system can reduce or remove an effect of Fluorescence or absorption on the measured signal, thereby isolating or improving the Raman signal ($R_0$).

Fluorescence

A challenge in the implementation of Raman spectroscopy to obtain physiological data is the emission of fluorescence. Accordingly, if fluorescence is generated, it often overwhelms the Raman signal, effectively hiding the Raman features. Thus, in some cases, is can be advantageous to isolate the Raman signal.

Figure 6:
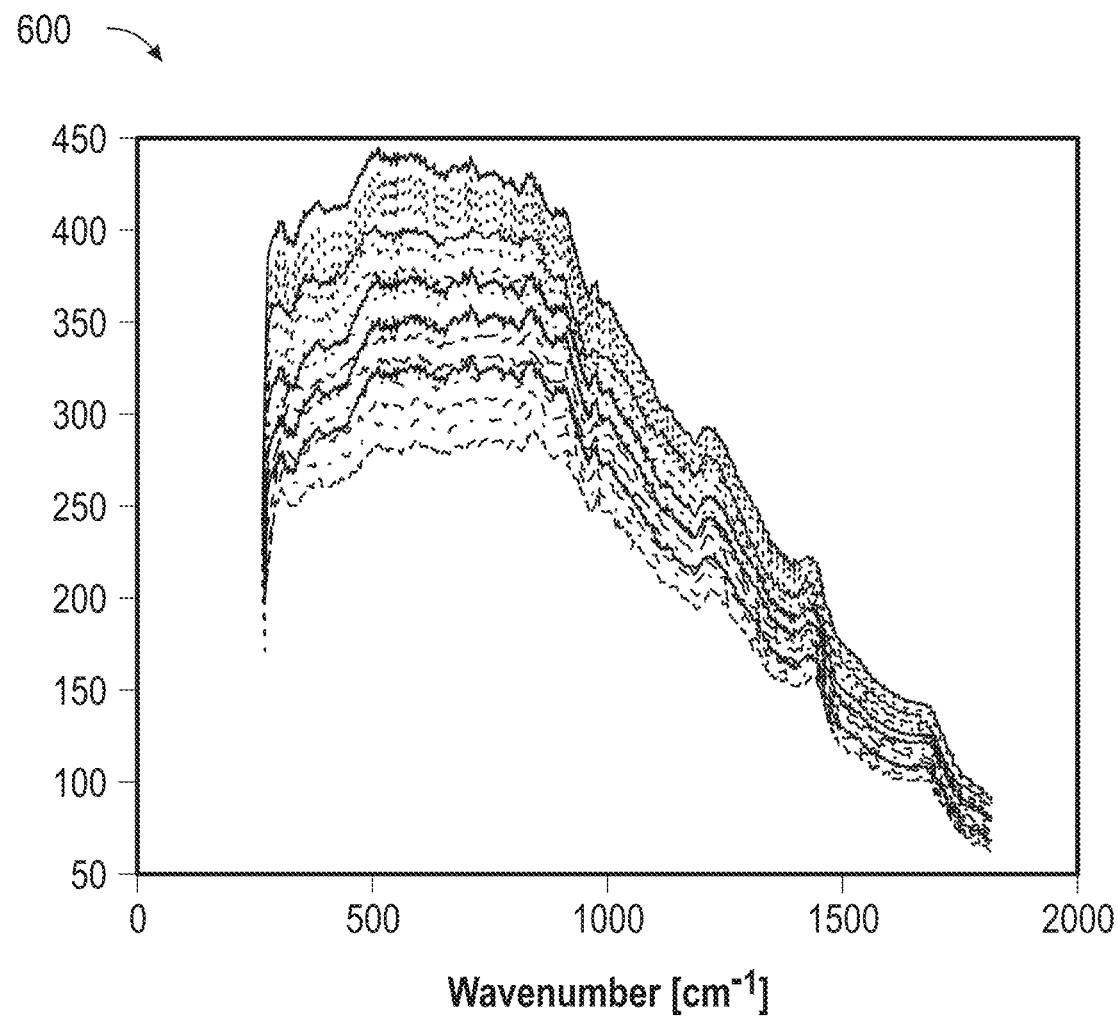
FIG. 6 shows a graph illustrating various example light intensity signals acquired at a patient's wrist.

FIG. 6 shows a graph 600 illustrating various example light intensity signals acquired at a patient's wrist. In this example, the y-axis corresponds to arbitrary intensity units, while the x-axis corresponds to a wavenumber shift (in $cm^{-1}$). Because the Raman signal is dependent on the excitation wavelength, it can be convenient to use wavenumber to indicate the change of wavelength compared to excitation wavelength. Wavelength change is also photo energy change that is often described by wavenumber change in the frequency domain, because wavenumber is used to describe wavelength in the frequency domain. Wavelength can convert to wavenumbers by dividing one centimeter by wavelength.

As described herein, the light intensity signal acquired from a Raman spectrometer is influenced by the emission of florescence. For example, fluorescence is often much more intense than Raman scattering, and fluorescence can overwhelm or mask a Raman measurement in the light intensity signal. This can be seen in each of the signals of the graph 600. For example, the overall shape of each signal of the graph 600 is attributable to the fluorescence, while the subtle oscillations of each signal are attributable to Raman. Because the fluorescence tends to mask the Raman spectrum, it can be desirable to remove or reduce an effect of the fluorescence on the light intensity signal.

Various techniques for removing or reducing an effect of the fluorescence on the light intensity signal are known, including, but not limited to, confocal configuration, photobleaching, chemical bleaching, deployment of laser excitation at longer wavelengths, filtering with respect to pixel frequency (or wavenumber frequency), signal decomposition by various forms of component subtraction from a priori information, photobleaching curve fitting to subtract away an approximated fluorescence signal, frequency offset Raman methods, spatial offset Raman methods, or the like.

For example, irradiating tissue with intense laser light for a long period of time (sometimes referred to as photobleaching) can reduce a level of fluorescence emission in the light intensity signal, thus increasing the signal to noise (S/N) ratio of a Raman measurement. That is because the fluorescence signal of skin will decrease over time (experiencing an exponential decay) as a source is continually shining, while a Raman signal will not change. By looking at the exponential decay (in time) of photobleaching, the system can obtain a fluorescence approximation by curve fitting.

As another example, a system can use a first excitation wavelength to characterize the fluorescence, and then can subtract the fluorescence from a signal of a second excitation wavelength to isolate the Raman. For example, a location of peaks of the fluorescence emission are independent of excitation wavelength, whereas a location of peaks and compactness of emission of Raman spectra are dependent on excitation wavelength. Using this information, the system can remove or reduce an effect of fluorescence emission in the light intensity signal. Fluorescence can also be removed by taking sequential measurements of the tissue over time.

For example, the fluorescence signal can be isolated by the change of the measured spectrum overtime.

Figure 7:
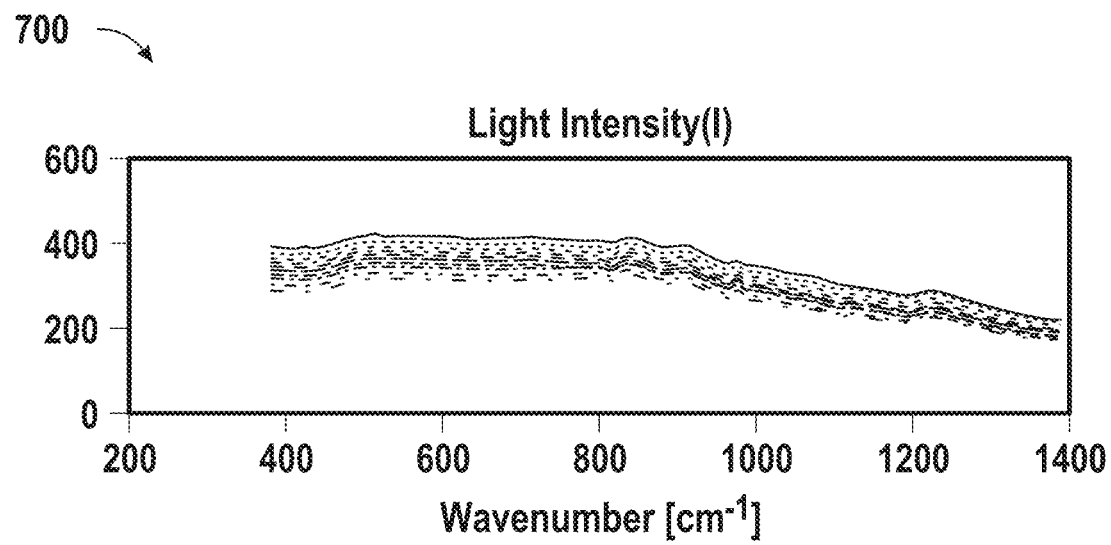
FIG. 7 illustrates a scaled view of the various example light intensity signals of FIG. 6.

FIG. 7 illustrates a scaled view of the various example light intensity signals of FIG. 6. As described herein with respect to FIG. 6, the light intensity signals are influenced by, among other things, fluorescence, Raman scattering, and tissue absorption. For example, the light intensity signals can include a significant fluorescence baseline.

Figure 8:
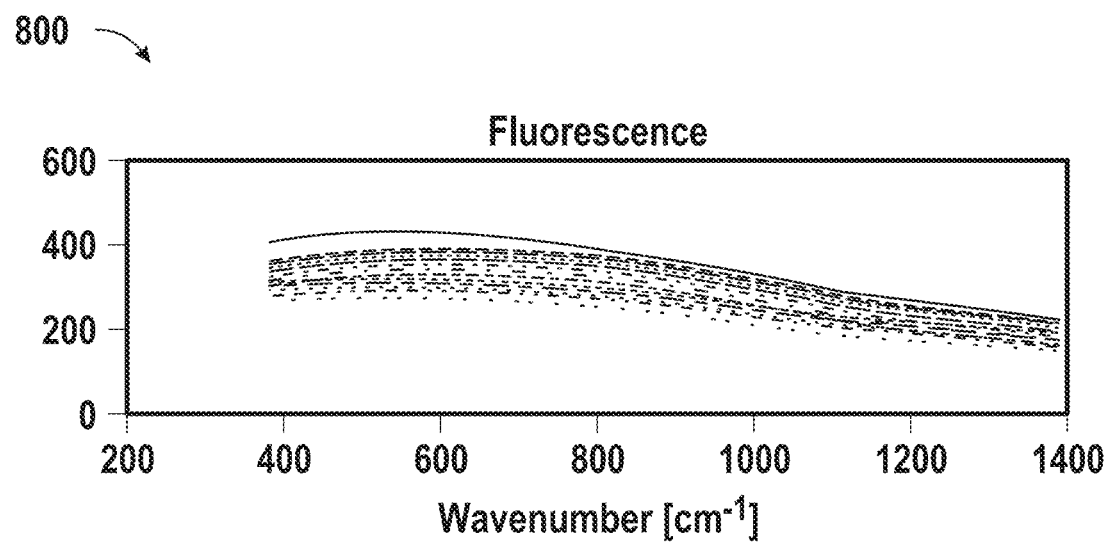
FIG. 8 illustrates an approximation of an intensity of the fluorescence portion of the light intensity signals of FIG. 7.

FIG. 8 illustrates an approximation of an intensity of the fluorescence portion 800 of the light intensity signals 700 of FIG. 7. This approximation of fluorescence can be determined using various techniques, such as those described herein. The system can utilize photobleaching curve fitting to subtract away an approximated fluorescence signal. For example, over time, the Raman signal ($R_0$) will remain constant while the fluorescence $F_0$ will experience an exponential decay. By looking at the exponential decay (in time) of photobleaching, the system can obtain a fluorescence approximation by curve fitting.

Figure 9:
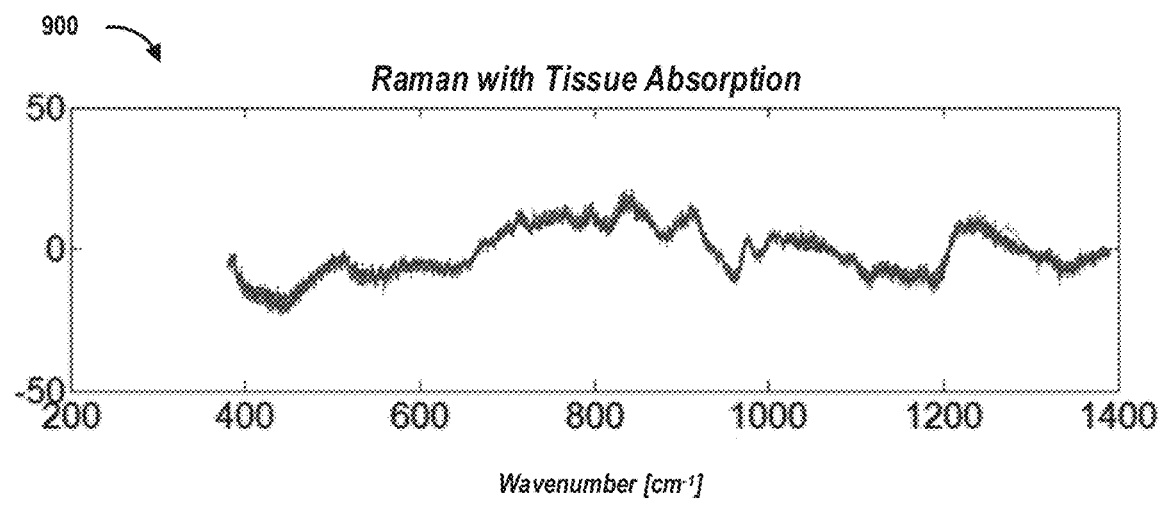
FIG. 9 illustrates an approximation of an intensity of the isolated Raman with tissue absorption signals of FIG. 7.

FIG. 9 illustrates an approximation of an intensity of the isolated Raman with tissue absorption signals of FIG. 7. In this example, at least some of the effect of florescence (for example, illustrated in FIG. 8) has been removed or reduced. Accordingly, the graph 700 of FIG. 7 can be approximately equal to the Raman and tissue absorption portion (for example, the $\Sigma(R_0 e^{-A_2})$ portion of Equation 6) of the light intensity signals of FIG. 6. As can be seen from a comparison of FIGS. 7 and 9, the presence of fluorescence in the light intensity signals 700 can mask many of the Raman features, such as the peaks, valleys, amplitude, compaction, and the like. By removing or reducing the presence of fluorescence in the light intensity signals 700, the system can isolate the Raman signal.

Figure 10:
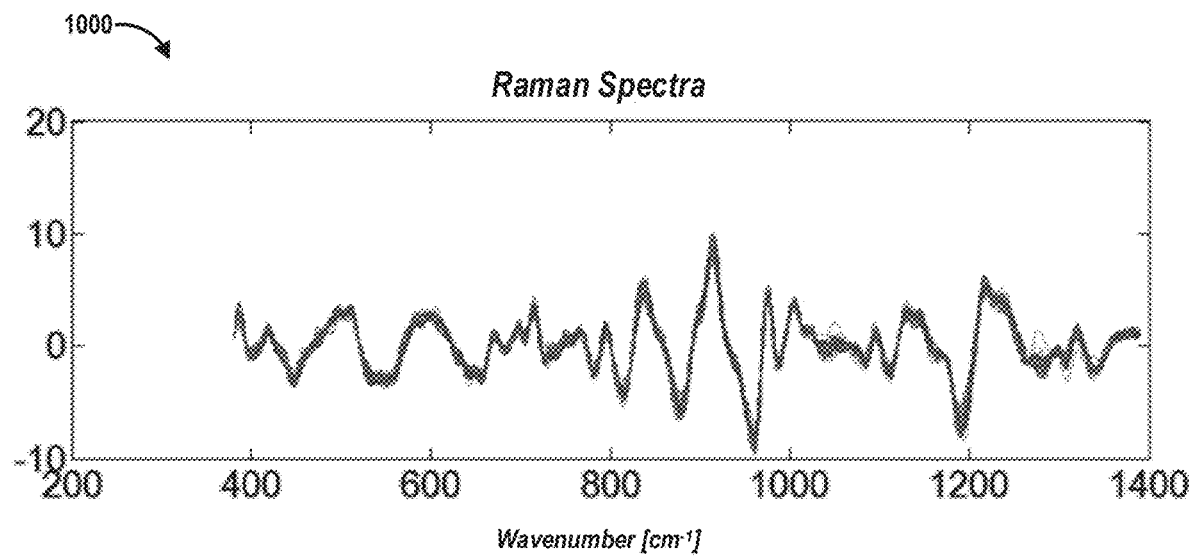
FIG. 10 illustrates an approximation of an intensity of the isolated Raman with tissue absorption signals of FIG. 7.

FIG. 10 illustrates an approximation of an intensity of the isolated Raman with tissue absorption signals of FIG. 7. In this example, the signal of graph 900 of FIG. 9 has been filtered to reduce or remove at least some of a remaining effect of florescence. For example, the system can filter the signal using a band pass or high pass filter.

Absorption

Another challenge in the implementation of Raman spectroscopy to obtain physiological data is the attenuation of the signal due to absorption. In some cases, the Raman signal can be isolated or improved by reducing or removing an effect of absorption on the measured signal. For example, sensor data from one or more sensors, such as a near infrared (NIR), reflectance, transmittance, or pulse oximetry sensor, can be utilized to determine absorption, which can be removed from one or more other measurements, such as a Raman measurement.

An effect of the tissue absorption (for example, the $e^{-A}$ portion of Equation 6) may be removed or reduced in various ways. For example, the absorption data, transmission data, reflectance data, or the like may be determined using data from one or more sensors, such as, but not limited to, a near infrared (NIR), reflectance, transmittance, or pulse oximetry sensor. Based on the sensor data, a processor can further process the signal (for example, signal 900 or 1000) to reduce or subtract an effect of the attenuation of the signal due to absorption.

Tissue Geometry

Figure 11A:
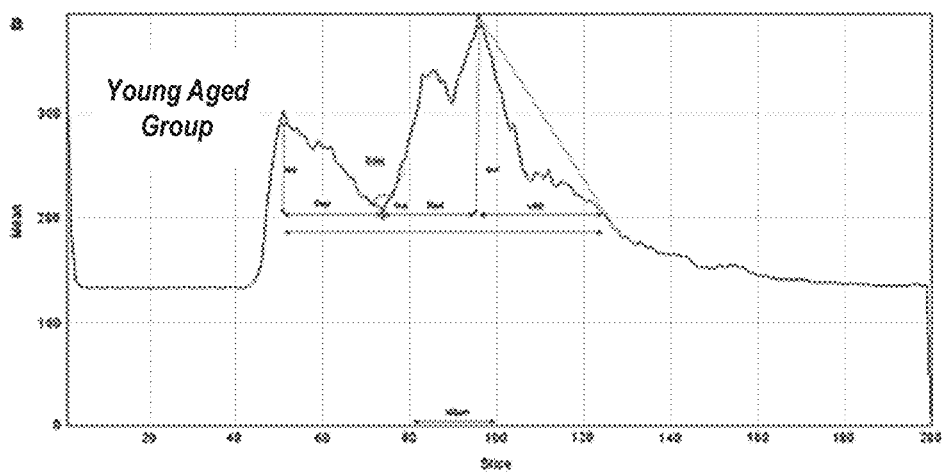
FIGS. 11A-11C illustrate optical scattering differences in skin geometries among various age groups.
Figure 11B:
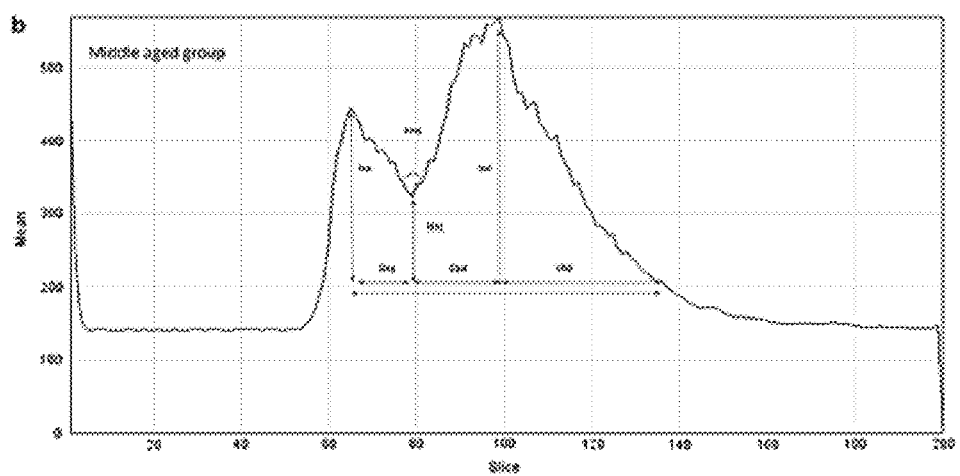
Figure 11C:
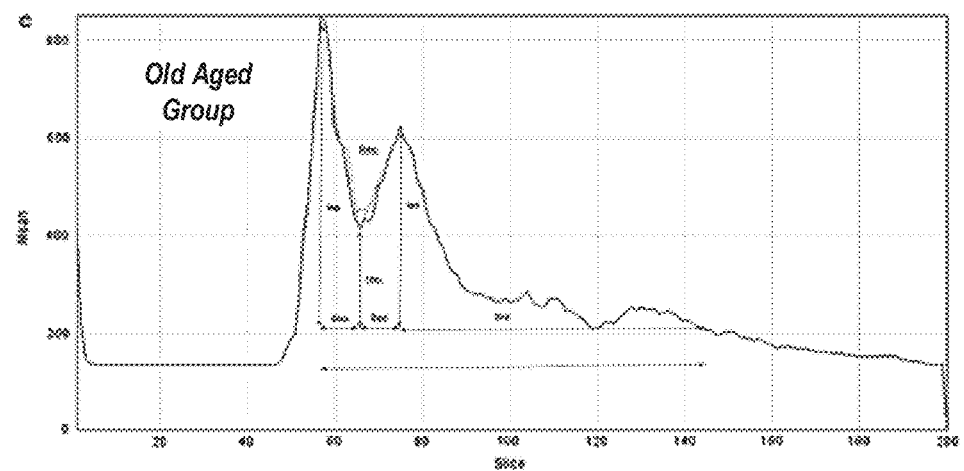

Tissue geometry can vary greatly between individuals. For example, skin structure or skin thickness can vary across races, ages, or the like. Even individuals having similar demographics can have different skin geometries. FIGS. 11A-11C illustrate optical scattering differences in skin geometries among various age groups. FIG. 11A corresponds to 20-39 year olds, FIG. 11B corresponds to 40-59 year-olds, and FIG. 11C corresponds to 60-79 year-olds. In these examples, the x-axis corresponds to a compaction of the skin and is measured from 0 to 200 units, where one unit is 3 µm, and the y-axis corresponds to brightness (for example, backscattered intensity) of the skin and is measured from 0 to 800 AU (absorbance units). As evidenced by these graphs 1100A, 1100B, 1100C, the general skin structure or thickness is not constant throughout the population.

Tissue geometry can be can also vary greatly between tissue sites of a particular individual. For example, each of a finger, a thumb, a thenar space of a hand, a wrist, a forearm, a nose, an ear, a neck, or other tissue site can have a different skin geometry. Even tissue sites that are in close proximity, such an upper part of a finger and a lower part of a finger, can have a different skin geometry.

Example Sensor Fusion Apparatus

A patient monitoring system such as systems 100 or 200 can include multiple noninvasive sensors. At least one sensor can be configured to provide tissue geometry information, and the system can utilize tissue geometry data to calibrate one or more other sensors or otherwise improve data obtained by the one or more other sensors. Techniques for utilizing sensor data to improve or calibrate another sensor can be referred to as data harmonization or sensor fusion.

As described herein, data acquired by a sensor can be a function of, or at least affected by, the tissue geometry of the particular tissue site that the sensor is interrogating. For example, tissues having a different geometry can result in a different optical profile. Consequently, data obtained from a first sensor at a first tissue site might not be useful for calibrating or improving a sensor that is interrogating a second, different tissue site. Accordingly, to accurately or reliably harmonize data between sensors, it can be helpful for each of the multiple sensors to acquire data associated with the same or a similar tissue site. In other words, it can be advantageous for each of the multiple sensors to interrogate the same or a sufficiently proximate tissue site so that a variable or other information determined using data from one sensor can be used to improve one or more others sensors. The present disclosure can provide for an apparatus configured allow multiple sensors to interrogate the same or a sufficiently proximate tissue site.

Figure 12A:
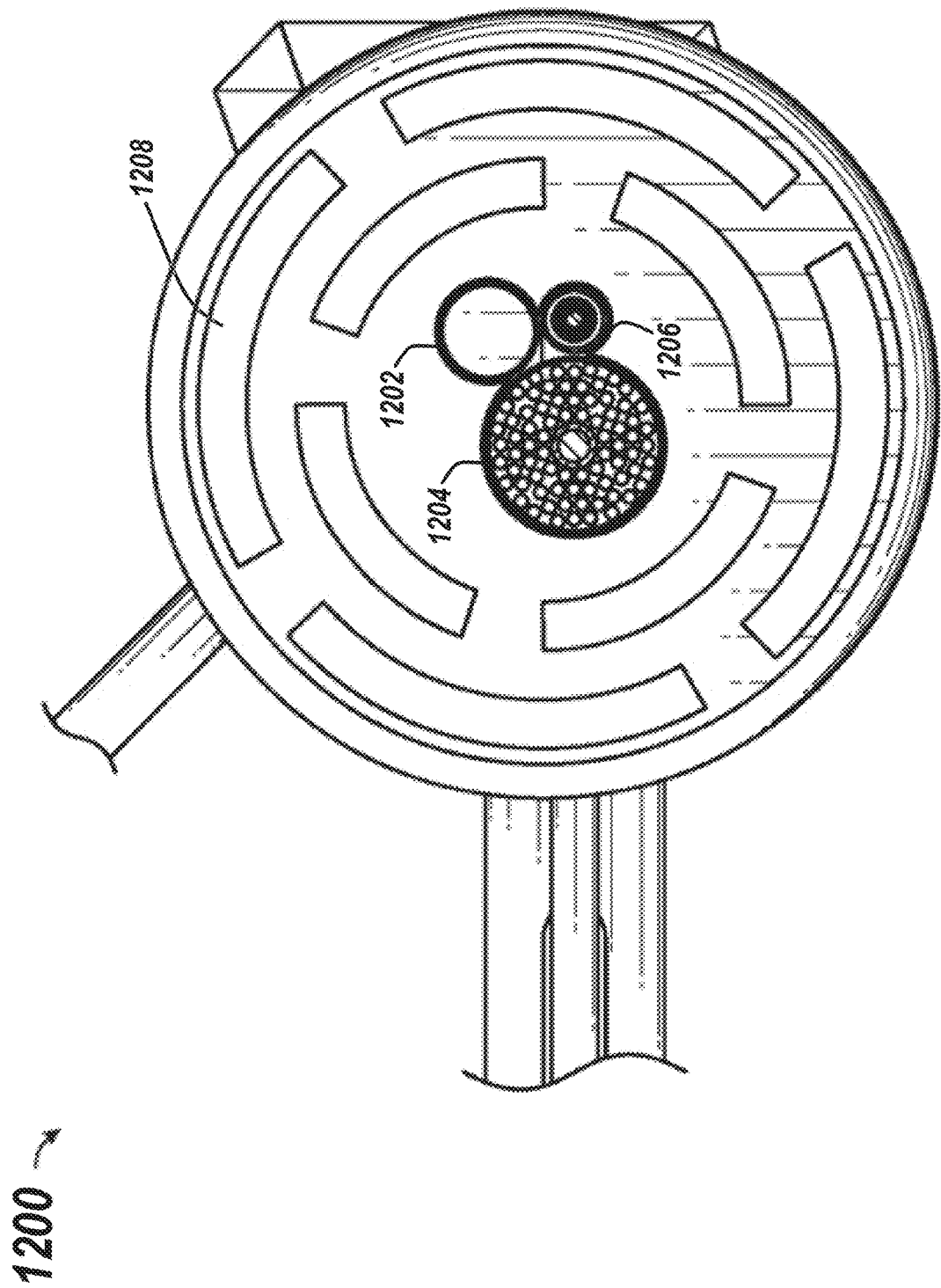
FIGS. 12A-12B illustrate an example sensor fusion apparatus configured with multiple sensing capabilities that interrogation of the same or a sufficiently proximate tissue site.
Figure 12B:
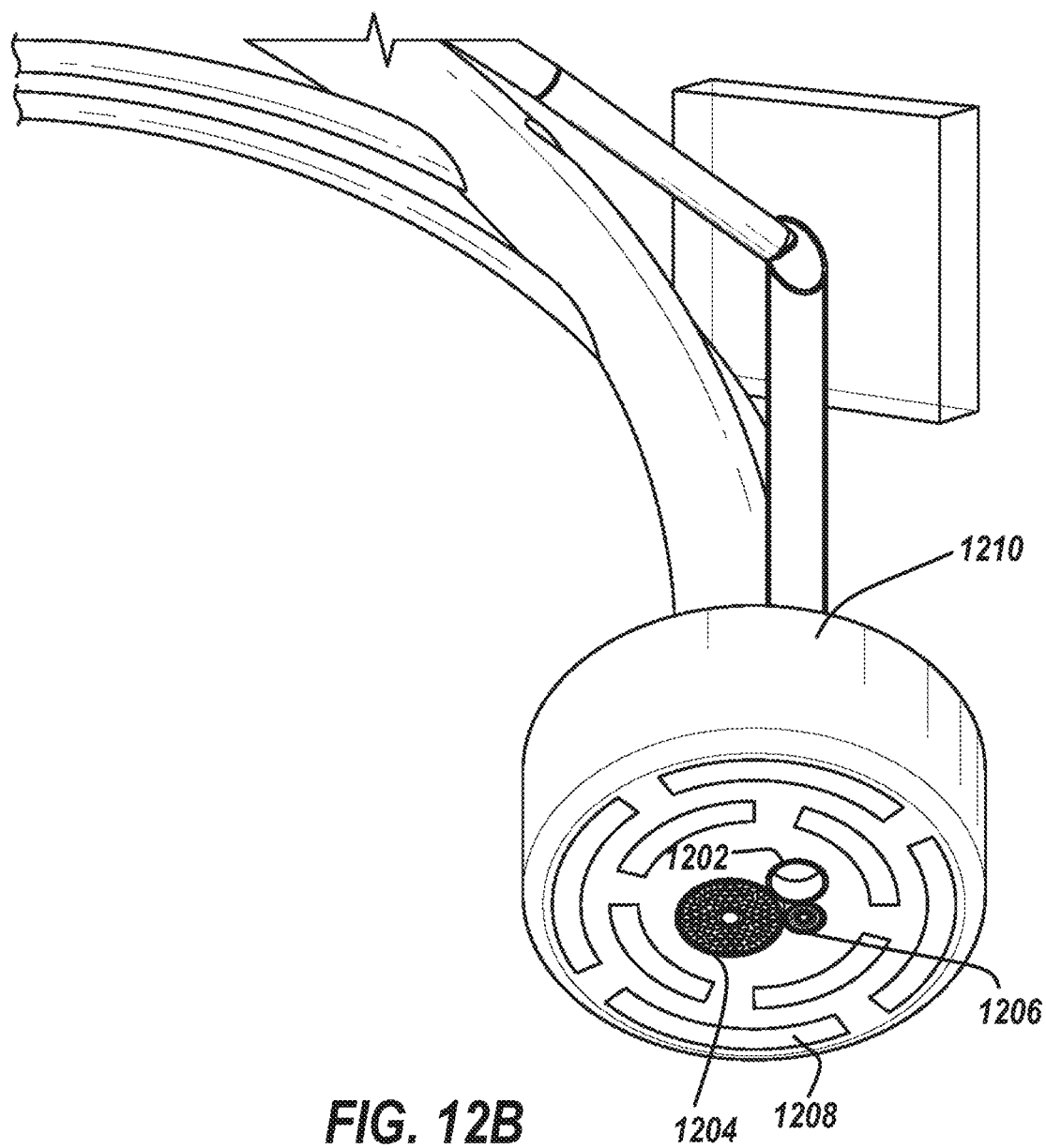

FIGS. 12A-12B illustrate an example sensor fusion apparatus 1200 configured with multiple sensing capabilities for interrogation of the same or a sufficiently proximate tissue site. As shown, the apparatus 1200 can include an OCT sensor or lens 1202, a Raman spectrometer 1204, a pulse oximetry sensor 1206, and a bioimpedance sensor 1208.

As illustrated in FIG. 12B, the apparatus 1200 can include a cylindrical housing 1210. In the illustrated example, the sensor side of the apparatus 1200 can be positioned on or proximate to a tissue site of a patient, and one or more of the an OCT sensor 1202, a Raman spectrometer 1204, a pulse oximetry sensor 1206, and a bioimpedance sensor 1208 can be configured to interrogate the same or a sufficiently proximate tissue site. Although at least some of the sensors are illustrated as being configured to obtain data via reflectance technologies, in some cases one or more sensors are configured to obtain data via transmittance or other technologies.

Example Reflectance Sensor

Figure 13:
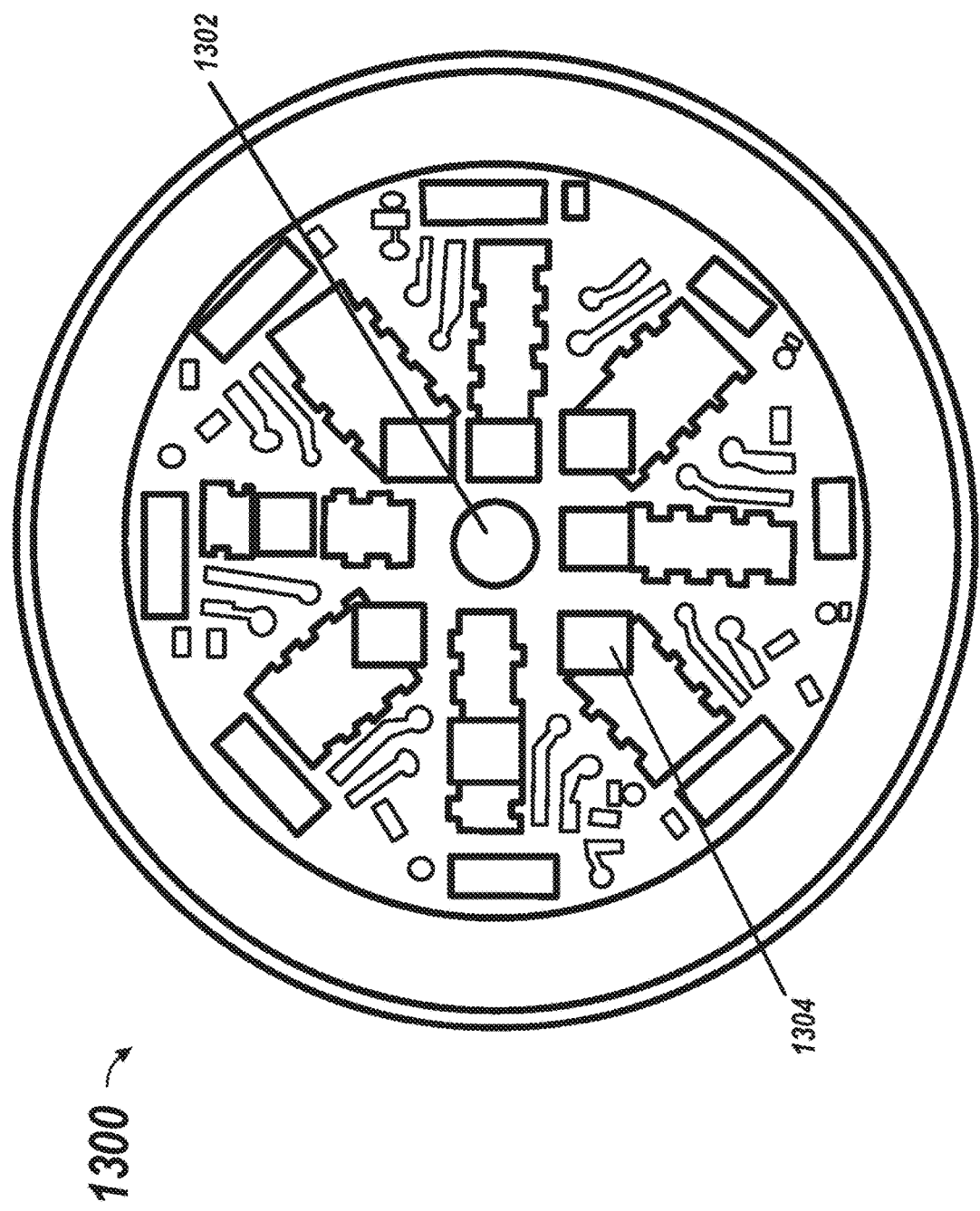
FIG. 13 illustrates an example reflectance sensor or probe.

FIG. 13 illustrates an example reflectance plethysmography sensor or probe 1300. The reflectance sensor or probe 1300 includes a light source 1302 at its center and seven detector channels 1304 surrounding the light source 1302.

The light source 1302 and emit light to illuminate a tissue site, and one or more of the channels 1304 can detect the light after it interacts with the tissue site. In some cases, the one or more of the channels 1304 can generate a composite analog light intensity signal responsive to the detected light. In some cases, light source 1302 or the channels 1304 can include a fiber-optic component for illumination or collection. For example, the light source 1302 can include a fiber bundle.

Figure 14:
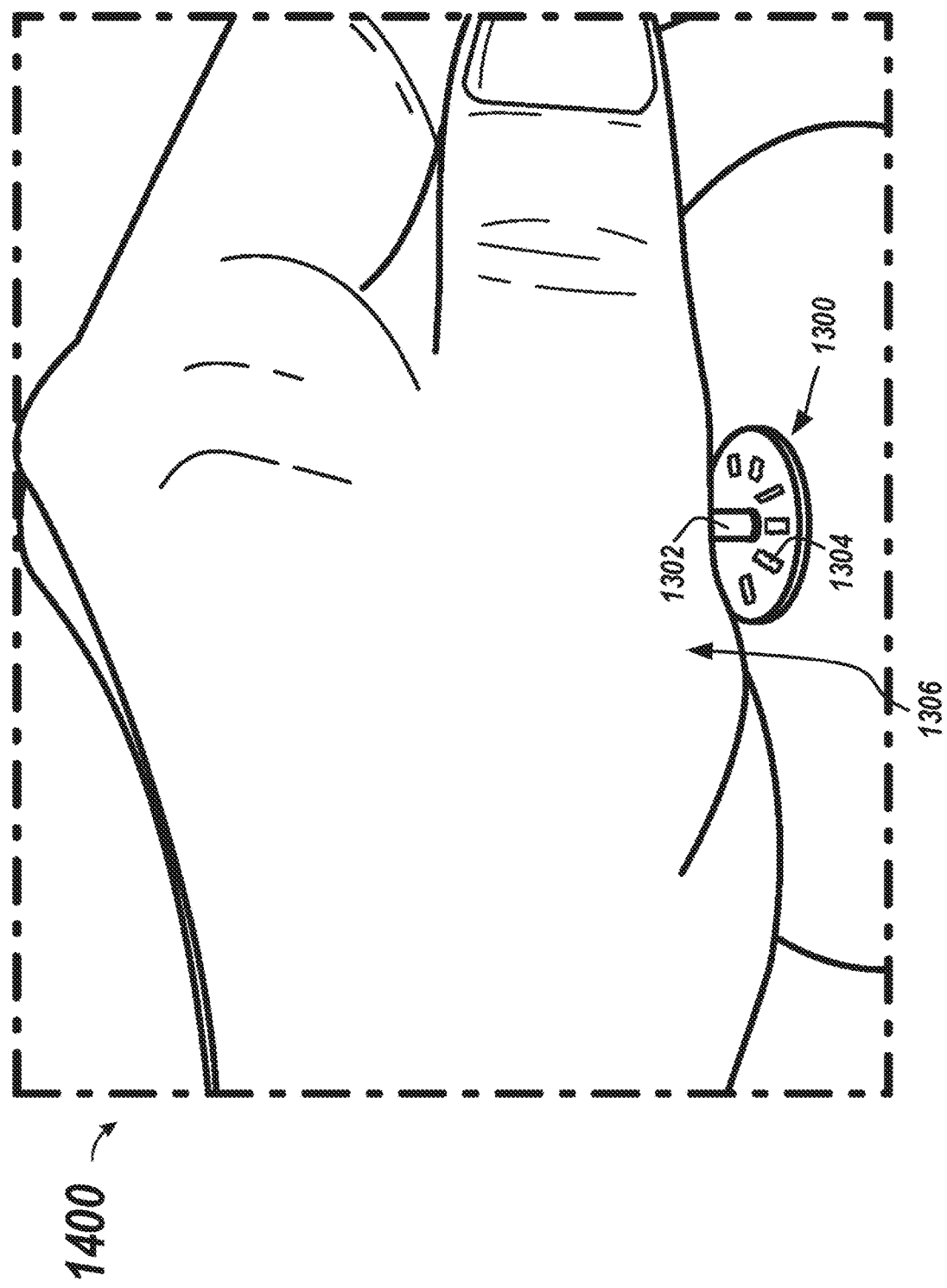
FIG. 14 illustrates an environment that shows a hand of a user interacting with the example reflectance sensor of FIG. 13.

FIG. 14 illustrates an environment 1400 that shows a hand of a user interacting with the example reflectance sensor 1300 of FIG. 13. The reflectance sensor 1300 can be configured to interact with one or more of the various tissue sites described herein. For example, as illustrated, the reflectance sensor 1300 can be positioned to interrogate at a metacarpal bone 1306. The metacarpal bone 1306 forms the intermediate part of the skeletal hand located between the phalanges of the fingers and the carpal bones of the wrist which forms the connection to the forearm.

Example Patient Monitoring

Figure 15:
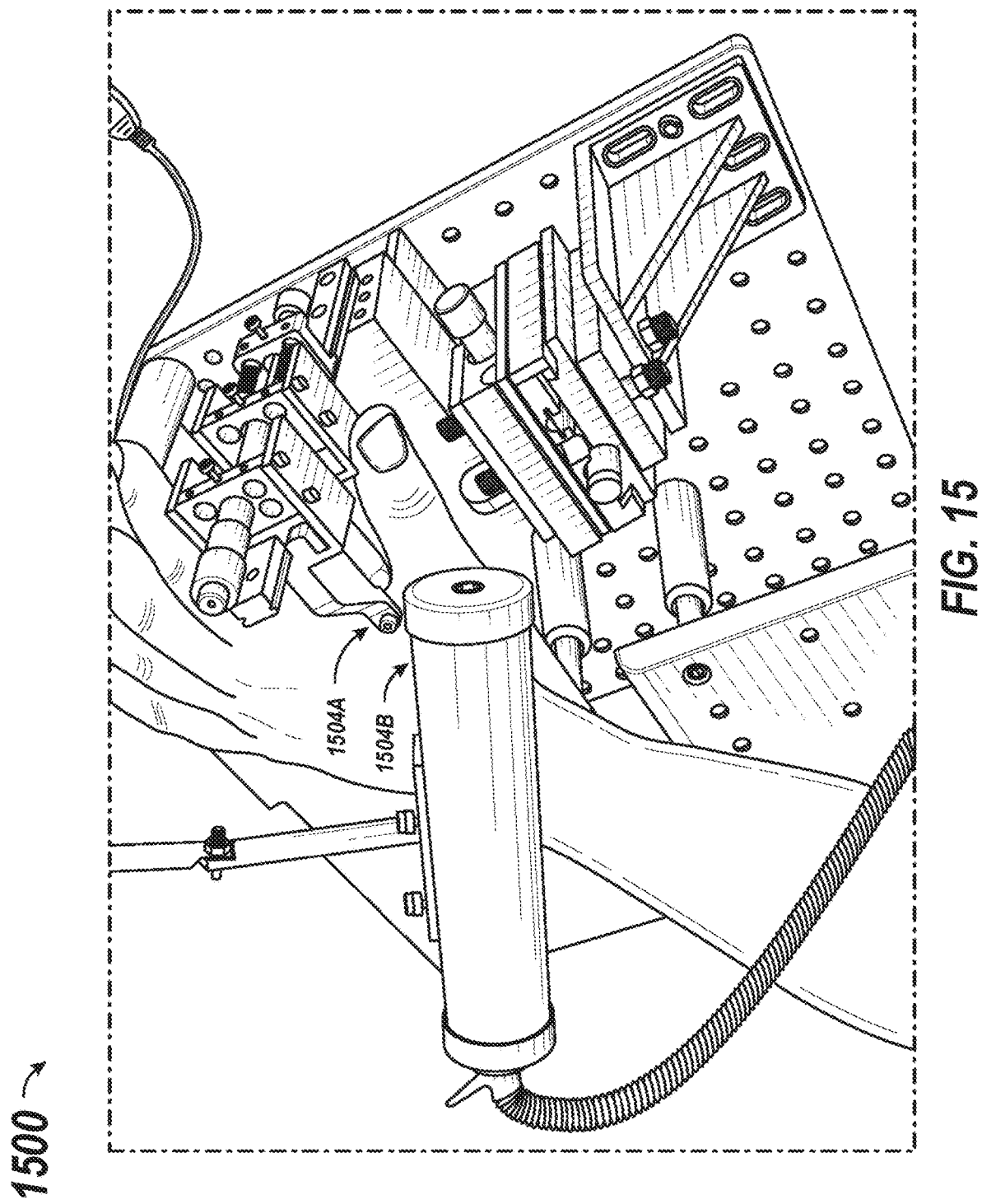
FIG. 15 illustrates an example physiological monitoring system.

FIG. 15 illustrates an example physiological monitoring system 1500, which can be an embodiment of the patient monitoring system 100 or 200. As illustrated in FIG. 15, the system 1500 can include a first sensor 1504A and a second sensor 1504B. In some implementations, the first sensor 1504A, the second sensor 1504B, or another sensor can be integrated into an apparatus, such as a wearable apparatus like a glove, a sock, an armband, a headband, a chest strap, etc.

The first sensor 1504A can be similar to sensor 204A, as described herein with respect to FIG. 2. For example, the sensor 1504A can include an emitter and detector. The emitter can emit light (for example, of an infrared or near-infrared wavelength) to illuminate a tissue site of a patient. In this example, the tissue site corresponds to a thenar space of the patient's hand. However, other tissue sites are contemplated. As the light interacts with (for example, passes through) the thenar space of the hand, some light may absorbed, reflected, refracted, or the like. The detector can receive or generate a signal responsive to the light detected by the detector after it interacts with the thenar space of the hand. The signal generated by the detector can be received by a processor (not shown), which can determine one or more various physiological parameters, such as an absorbance of the tissue based at least in part on the received signal.

The second sensor 1504B can be similar to sensor 204C, as described herein with respect to FIG. 2. For example, the second sensor 1504B can include a light source and a detector. The emitter can emit light (for example, of an infrared or near-infrared wavelength) to illuminate a tissue site of a patient. As the light interacts with (for example, reflects off) the thenar space of the hand, some light may absorbed, transmitted through, reflected, refracted, or the like. The detector can receive or generate a signal responsive to the light detected by the detector after it interacts with the hand. The signal generated by the detector can be received by a processor (not shown), which can determine one or more various physiological parameters, such as a transmittance of the tissue based at least in part on the received signal.

Figure 16A:
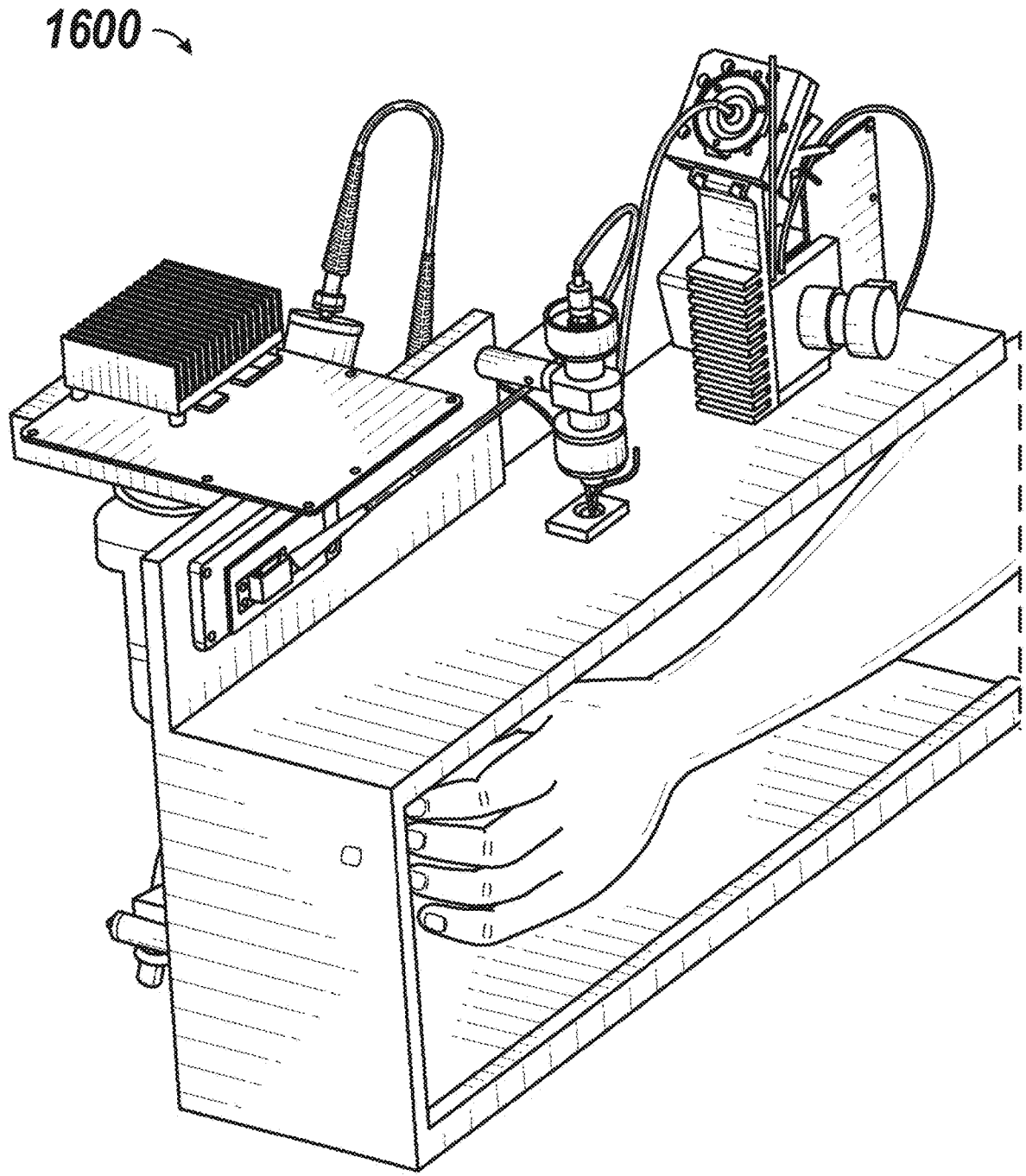
FIGS. 16A-16C illustrate an example physiological monitoring apparatus.
Figure 16B:
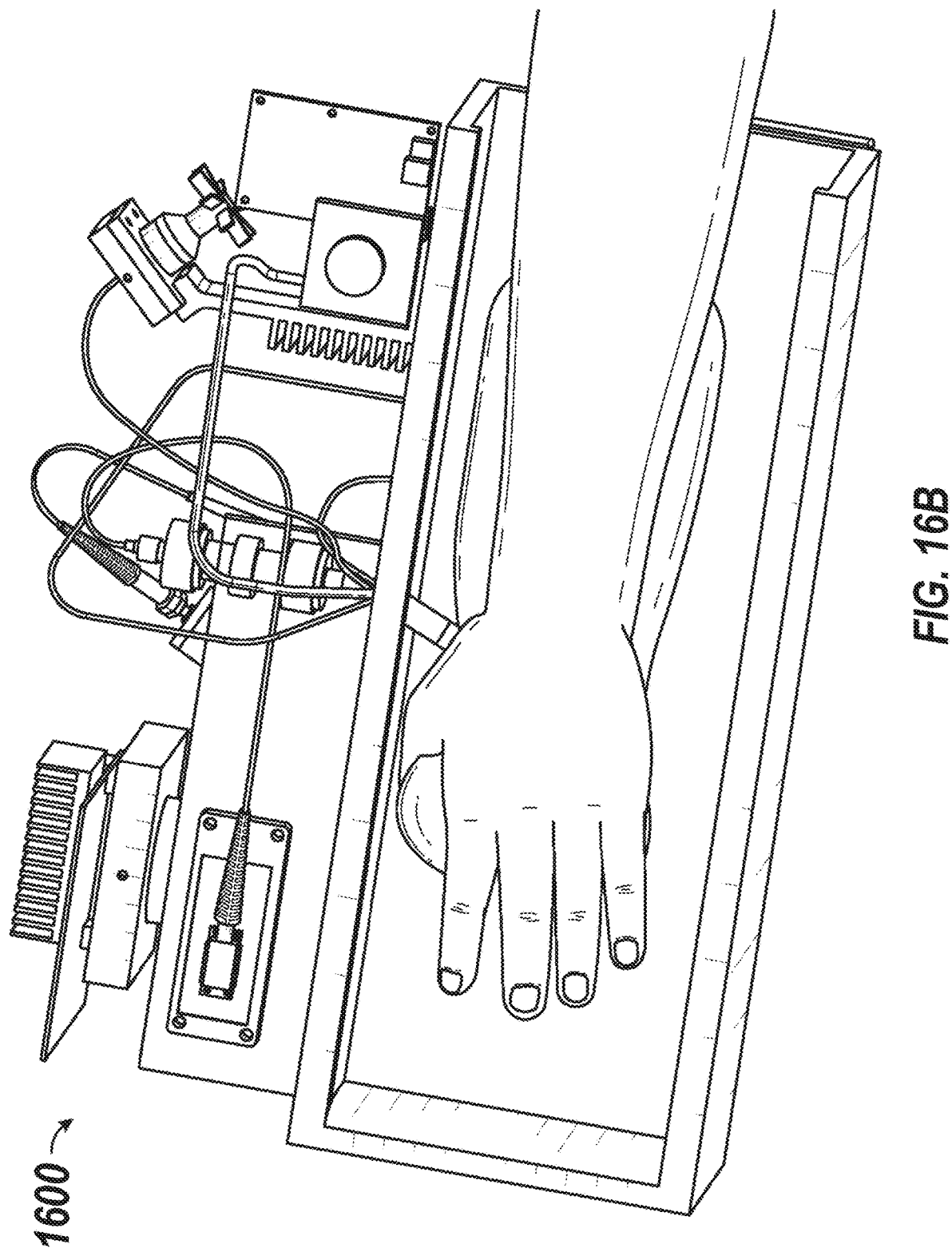
Figure 16C:
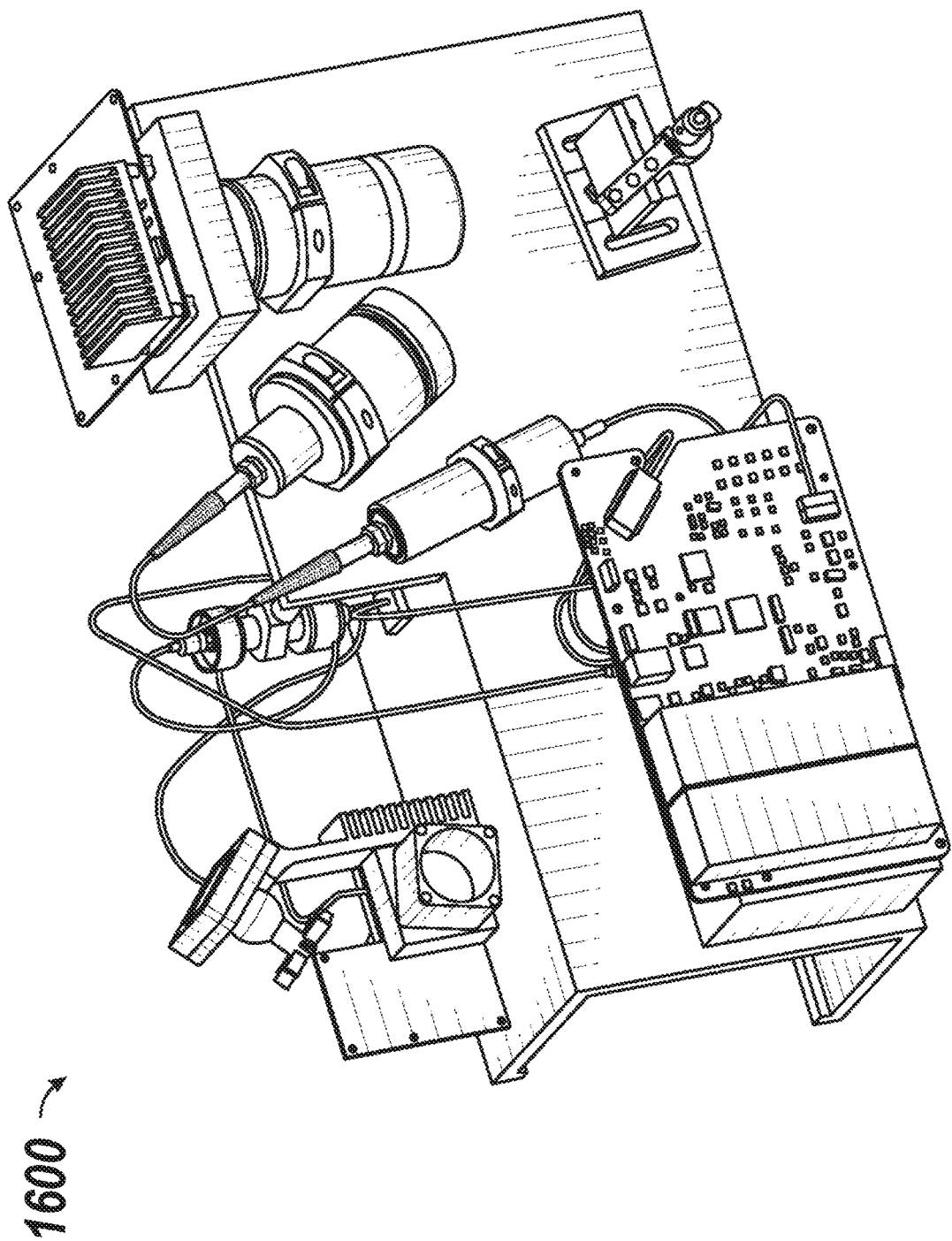

FIGS. 16A-16C illustrate an example physiological monitoring apparatus 1600. As illustrated, a user can place his or her arm in the apparatus 1600, such that two or more sensors of the apparatus 1600 can interrogate tissue of the arm. The two or more sensors can correspond to any of the sensors described herein. For example, the two or more sensors can interrogate the same or a different tissue site of the arm. In some cases, the apparatus 1600 can be miniaturized and integrated into a wearable apparatus, such as a glove, a sock, an armband, a headband, a chest strap, etc.

Example Data Harmonization

Figure 17:
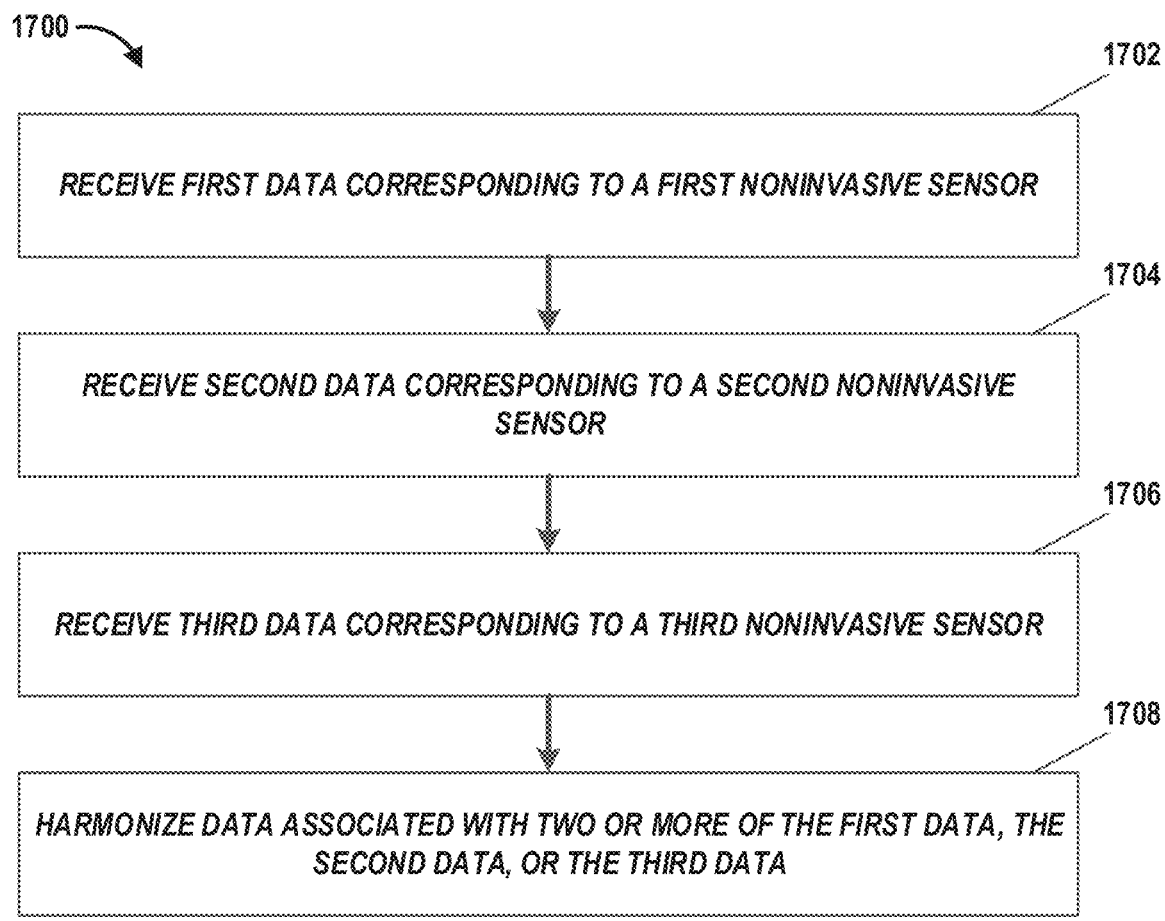
FIG. 17 illustrates a flow diagram illustrative of an example routine for harmonizing data from a plurality of non-invasive sensors.

FIG. 17 illustrates a flow diagram illustrative of an example routine for harmonizing data from a plurality of non-invasive sensors. One skilled in the relevant art will appreciate that the elements outlined for routine 1700 may be implemented by one or many computing devices/components, such as in hardware, with a front end component, with a sensor interface, or with a processor, such as one or more processors housed in a patient monitor, one or more remote processors, one or more processors housed in the sensors, etc. Accordingly, although routine 1700 has been logically associated as being generally performed by a processor, the following illustrative embodiments should not be construed as limiting.

At block 1702, a processor can receive data from one or more first noninvasive sensors. The one or more first noninvasive sensors can include an optical coherence tomography (OCT) sensor. As described herein, the OCT sensor can provide a non-invasive method for identifying one or more characteristics of a tissue's structure. The data received by the processor from the OCT sensor can include OCT data, which can be referred to as tissue geometry data.

In addition or alternatively, the one or more first noninvasive sensors can include a bioimpedance sensor or a tissue dielectric constant sensor. As described herein, the bioimpedance sensor or tissue dielectric constant sensor can provide a non-invasive method for identifying one or more characteristics of a tissue's structure. The data received by the processor from the bioimpedance sensor or tissue dielectric constant sensor can include bioimpedance data, which can include tissue geometry data, hydration data, or the like.

At block 1704, a processor can receive data from one or more second noninvasive sensors. The one or more second noninvasive sensors can include a pulse oximetry sensor, such as a reflectance or transmission sensor. As described herein, the pulse oximetry sensor can provide a non-invasive method for identifying or more of various physiological parameters.

At block 1706, a processor can receive data from one or more third noninvasive sensors. The one or more second noninvasive sensors can include a Raman spectrometer. As described herein, the Raman spectrometer can provide a non-invasive method for identifying or more of various physiological parameters.

At block 1708, the processor can harmonize the data received from two or more of the non-invasive sensors. By harmonizing the data from two or more non-invasive sensors, the system may be able to compensate for circumstances that might otherwise result in inaccurate or unreliable data. For example, using skin geometry information (for example, skin thickness), the processor can weight or prioritize longer or shorter path length detectors. In addition or alternatively, the various sensor data, such as skin geometry information, can allow the processor compensate for sensor or probe placement. For example, a location, coupling, or pressure can be compensated by the processor by adjusting path length, which can be determined from the various sensor data, such as skin geometry information. Similarly, the processor can utilize the various sensor data, such as skin geometry information, to detect drift or motion at the tissue site.

As a non-limiting example, the data received at block 1702 from the OCT sensor, the bioelectrical impedance sensor, or the tissue dielectric constant sensor can include tissue geometry information. Based at least in part on the tissue geometry data, the processor can determine a path length corresponding to a tissue site interrogated by the one or more first noninvasive sensors. In some cases, the determined path length can be utilized with the pulse oximetry sensor to determine a concentration of an analyte, such as blood glucose. For example, based on the data received at block 1704 from the one or more second noninvasive sensors, the processor can determine an absorbance corresponding to a tissue site interrogated by the one or more second noninvasive sensors. Using one or more relationships derived from Beer's law (Equation 1), the concentration, c, of one or more analytes can be determined using the absorbance, A, determined from the pulse oximetry sensor data, and the path length, b, determined from the tissue geometry data.

As another non-limiting example, the processor can utilize the tissue geometry data to select a focal depth or focal length, wavelength, refractive index, or other parameter associated with the Raman spectrometer. For example, the tissue geometry data can provide an indication of a particular location of tissue, such as the capillary beds. The processor can select a focal depth or focal length of the Raman spectrometer such that the Raman spectrometer can focus on this particular location. As a result, the processor can determine a more accurate indication of glucose concentration from the Raman signal.

As another non-limiting example, the processor can utilize the pulse oximetry data to filter data received from a Raman Spectrometer to isolate a Raman Spectra. For example, as described herein, a direct measurement of glucose can be determined based on features of the isolated Raman signal. Using the pulse oximetry data, the processor can filter out an effect of absorbance on the Raman Spectra.

In addition or alternatively, using the various sensor data, the processor can create calibrations for one or more individuals. For example, although skin geometry may vary between individuals, one or more groups of individuals may have similar skin geometries, which can allow for more accurate physiological parameter estimations of for individuals in those groups. For example, using the various sensor data, such as the skin geometry, Raman, or NIR data, the processor can determine calibrations for different groups, such as different skin populations, different ages, or the like.

The various blocks of process 1700 described herein can be implemented in a variety of orders, and that the system can implement one or more of the blocks concurrently or change the order, as desired. For example, the system 100 can concurrently receive any of the sensor data, or receive the sensor data in any order. Similarly, the system can make one or more calculations or determinations in any order, such as before or after receiving data from one or more sensors.

It will be understood that any of the first, second, or third sensors can interrogate the same or a different tissue site. Furthermore, it will be understood that fewer, more, or different blocks can be used as part of the routine 1700. Likewise, fewer, more, or different sensors can be used by the system. For example, the routine 1700 can include blocks for receiving data associated with additional non-invasive sensors or determining various other physiological parameters. Furthermore, the routine 1700 can include causing a display to display one or more of various indications of the any other the sensor data, calculations, or determinations.

Figure 18:
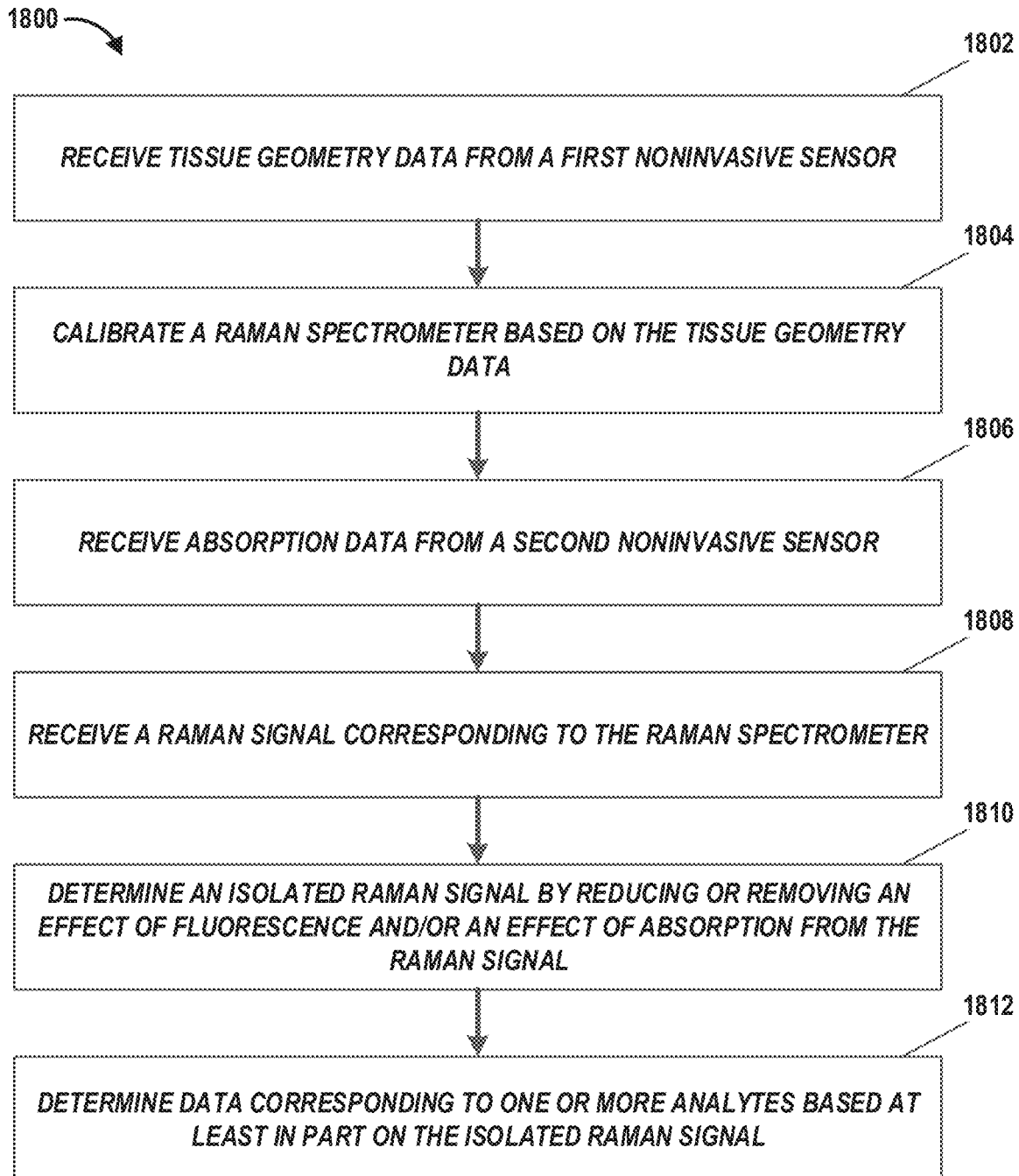
FIG. 18 illustrates a flow diagram illustrative of an example routine for harmonizing data from a plurality of non-invasive sensors.

FIG. 18 illustrates a flow diagram illustrative of an example routine for harmonizing data from a plurality of non-invasive sensors. One skilled in the relevant art will appreciate that the elements outlined for routine 1800 may be implemented by one or many computing devices/components, such as in hardware, with a front end component, with a sensor interface, or with a processor, such as one or more processors housed in a patient monitor, one or more remote processors, one or more processors housed in the sensors, etc. Accordingly, although routine 1800 has been logically associated as being generally performed by a processor, the following illustrative embodiments should not be construed as limiting.

At block 1802, the process 1800 can receive tissue geometry data from a first noninvasive sensor. As described herein, the first non-invasive sensor can include a combination of one or more of an OCT sensor, a bioimpedance sensor, a tissue dielectric constant sensor, or any other sensor configured to measure or determine tissue geometry data. The tissue geometry data can include various information corresponding to the skin, fluids, bones, or the like. For example, tissue geometry data can include, but is not limited to, a thickness of one or more skin layers (for example, the epidermis, the dermoepidermal junction, the papillary dermis, the reticular dermis, etc.), cellular structure information, a water content of a portion of the tissue, etc.

At block 1804, the process 1800 can calibrate a Raman Spectrometer based at least in part on the tissue geometry data received at block 1802. For example, the tissue geometry data can provide insight about the tissue site, which can allow the process 1800 to optimize one or more settings of the Raman spectrometer. For example, based at least in part on the tissue geometry data, the process 1800 can select a focal depth or focal length, wavelength, refractive index, or other parameter associated with the Raman spectrometer. By adjusting one or more settings or positioning of the Raman spectrometer based on the tissue geometry data, the process can enhance a signal received by the Raman spectrometer. For example, the new settings can increase the collection efficiency, the resolution, the signal-to-noise ratio, or the like of the Raman signal.

At block 1806, the process 1800 can receive absorption, transmission, reflectance, or other data from a second non-invasive sensor. As described herein, the second non-invasive sensor can include one or more of a pulse oximetry sensor, a reflectance sensor, a transmittance sensor, or another sensor from which absorption, transmission, reflectance, or other tissue related data can be determined. In some cases, the second noninvasive sensor can include a light source configured to emit light and a detector and configured to detect light. Depending on the type of sensors, the detected can be configured to detect light after having it has passed through, reflected, refracted, or scattered at a tissue site of a patient. In some cases, the tissue site corresponding to the second sensor (for example, the tissue site at which the second sensor takes a measurement) is the same tissue site (or within a close proximity) as the tissue site of the second sensor. For example, the first and second sensors can be configured to interrogate the tissue site at different periods of time. However, in some cases, the first and second sensors can be configured to interrogate different tissue sites.

At 1808, the process 1800 can receive a Raman signal corresponding to the Raman spectrometer. As described herein, the light intensity signal acquired from a Raman spectrometer is influenced by the emission of florescence.

At block 1810, the process 1800 can determine an isolated Raman signal by reducing or removing an effect of fluorescence or an effect of absorption from the Raman signal received at block 1808. As described herein, fluorescence can overwhelm or mask a Raman measurement in the light intensity signal. As such, the process 1800 can use one or more techniques described herein to reduce or remove an effect of the fluorescence on the Raman signal. In addition or alternatively, the process 1800 can reduce or remove an effect of absorption on the Raman signal. For example, using the absorption data acquired at block 1806, the process 1800 can filter, subtract, reduce, or remove an effect of absorption on the Raman signal. By reducing or removing an effect of fluorescence or an effect of absorption from the Raman signal, the process 1800 can determine an isolated (or semi-isolated) Raman signal.

At block 1812, the process 1800 can determine data corresponding to one or more analytes based at least in part on the isolated Raman signal. For example, features of the Raman spectra (such as peaks, valleys, concentrations, etc.) can corresponds to analytes such as glucose. Accordingly, using the isolated or semi-isolated Raman signal, the system can identify physiological data, such as information regarding a patient's blood glucose level. Thus, the process 1800 can harmonize data from various non-invasive sensors to non-invasively determine a patient's blood glucose level, or other analyte.

It will be understood that the various blocks of process 1800 described herein can be implemented in a variety of orders, and that the system can implement one or more of the blocks concurrently or change the order, as desired. Furthermore, it will be understood that fewer, more, or different blocks can be used as part of the routine 1800. For example, fewer, more, or different sensors can be used by the system. Furthermore, the routine 1800 can include blocks for receiving data associated with additional non-invasive sensors or determining various other physiological parameters. Furthermore, the routine 1800 can include displaying one or more of various indications of the any other the sensor data, calculations, or determinations.

Further Examples

Various example features can be found in the following clauses, which can be implemented together with any combination of the features described above:

Clause 1: A physiological monitoring system configured to determine a physiological parameter by harmonizing data between two or more different types of non-invasive physiological sensors interrogating the same or proximate measurement sites, the physiological monitoring system comprising:
  a first non-invasive sensing device of a first type configured to interrogate a tissue site of a patient and generate a first signal indicative of first physiological data associated with the tissue site;
  a second non-invasive sensing device of a second type that is different from the first type configured to interrogate the tissue site of the patient and generate a second signal indicative of second physiological data associated with the tissue site; and
  one or more processors in communication with the first and second non-invasive sensing devices, the one or more processors configured to:
    receive the first signal indicative of the first physiological data;
    receive the second signal indicative of the second physiological data; and
    determine a physiological parameter based at least in part on the first and second signals.

Clause 2: The system of Clause 1, wherein the first non-invasive sensing device comprises one or more of an optical coherence tomography (OCT) sensor, a bioimpedance sensor, or a tissue dielectric constant sensor.

Clause 3: The system of any of the previous clauses, wherein the first physiological data comprises tissue geometry data corresponding to the tissue site.

Clause 4: The system of any of the previous clauses, wherein tissue geometry data comprises at least one of data corresponding to one or more of a thickness of one or more layers of skin of the tissue site, cellular structure information associated with the tissue site, or a water content associated with the tissue site.

Clause 5: The system of any of the previous clauses, wherein the first non-invasive sensing device comprises a plethysmography sensor.

Clause 6: The system of any of the previous clauses, wherein the plethysmography sensor comprises one or more of a pulse oximetry sensor, a transmission plethysmography sensor, or a reflectance plethysmography sensor.

Clause 7: The system of any of the previous clauses, wherein the plethysmography sensor comprises:
  at least one emitter configured to emit light, and
  at least one detector configured to:
  detect the light after interaction with the tissue site, and
  generate the second signal responsive to the detected light.

Clause 8: The system of any of the previous clauses, wherein the first non-invasive sensing device and the second non-invasive sensing device are configured to simultaneously interrogate the tissue site.

Clause 9: The system of any of the previous clauses, wherein the first non-invasive sensing device and the second non-invasive sensing device are configured to interrogate the tissue site at distinct and different time periods.

Clause 10: The system of any of the previous clauses, wherein the second non-invasive sensing device comprises a Raman spectrometer.

Clause 11: The system of any of the previous clauses, wherein the second physiological data corresponds to Raman spectra associated with the tissue site.

Clause 12: The system of any of the previous clauses, wherein the one or more processors are further configured to determine an isolated Raman signal by reducing or removing at least one of an effect of fluorescence or an effect of absorption from the second signal.

Clause 13: The system of any of the previous clauses, wherein the one or more processors are further configured to determine the isolated Raman signal based at least in part on the first signal.

Clause 14: The system of any of the previous clauses, wherein the one or more processors are further configured to determine a path length associated with the tissue site based at least in part on the first signal, wherein the determination of the physiological parameter is based at least in part on the determined path length.

Clause 15: The system of any of the previous clauses, wherein the one or more processors are further configured to determine an absorption of light of the tissue site based at least in part on the second signal, wherein the determination of the physiological parameter is based at least in part on the determined absorption of light.

Clause 16: The system of any of the previous clauses, wherein physiological parameter comprises a concentration of one or more analytes.

Clause 17: The system of any of the previous clauses, wherein physiological parameter comprises a blood glucose concentration associated with the tissue site.

Clause 18: The system of any of the previous clauses, wherein one or more processors are further configured to calibrate the second non-invasive sensing device based at least in part on the first signal.

Clause 19: The system of any of the previous clauses, wherein second non-invasive sensing device comprises a Raman spectrometer, wherein to calibrate the Raman spectrometer, the one or more processors are configured to select at least one of a focal depth, a focal length, a wavelength, or a refractive index, associated with the Raman spectrometer.

Clause 20: The system of any of the previous clauses, wherein the tissue site comprises a thenar space of a hand.

Clause 21: The system of any of the previous clauses, wherein the tissue site comprises an area associated with a metacarpal bone.

Clause 22: A method for determining a physiological parameter by harmonizing data between two or more different types of non-invasive physiological sensors interrogating the same or proximate measurement sites, the method comprising:
  receiving a first signal from a first non-invasive sensing device of a first type, wherein the first non-invasive sensing device is configured to interrogate a tissue site of a patient and generate the first signal, wherein the first signal is indicative of first physiological data associated with the tissue site;
  receiving a second signal from a second non-invasive sensing device of a second type that is different from the first type, wherein the second non-invasive sensing device is configured to interrogate the tissue site of the patient and generate the second signal, wherein the second signal is indicative of second physiological data associated with the tissue site; and/or determining a physiological parameter based at least in part on the first and second signals.

Clause 23: The method of Clause 22, wherein the first non-invasive sensing device comprises one or more of an optical coherence tomography (OCT) sensor, a bioimpedance sensor, or a tissue dielectric constant sensor.

Clause 24: The method of any of Clauses 22 or 23, wherein the first physiological data comprises tissue geometry data corresponding to the tissue site.

Clause 25: The method of any of Clauses 22-24, wherein tissue geometry data comprises at least one of data corresponding to one or more of a thickness of one or more layers of skin of the tissue site, cellular structure information associated with the tissue site, or a water content associated with the tissue site.

Clause 26: The method of Clauses 22-25, wherein the first non-invasive sensing device comprises a plethysmography sensor.

Clause 27: The method of Clauses 22-26, wherein the plethysmography sensor comprises one or more of a pulse oximetry sensor, a transmission plethysmography sensor, or a reflectance plethysmography sensor.

Clause 28: The method of Clauses 22-27, wherein the plethysmography sensor comprises:
  at least one emitter configured to emit light, and
  at least one detector configured to:
    detect the light after interaction with the tissue site, and
    generate the second signal responsive to the detected light.

Clause 29: The method of Clauses 22-28, wherein the first non-invasive sensing device and the second non-invasive sensing device are configured to simultaneously interrogate the tissue site.

Clause 30: The method of Clauses 22-29, wherein the first non-invasive sensing device and the second non-invasive sensing device are configured to interrogate the tissue site at distinct and different time periods.

Clause 31: The method of Clauses 22-30, wherein the second non-invasive sensing device comprises a Raman spectrometer.

Clause 32: The method of Clauses 22-31, wherein the second physiological data corresponds to Raman spectra associated with the tissue site.

Clause 33: The method of Clauses 22-32, further comprising determining an isolated Raman signal by reducing or removing at least one of an effect of fluorescence or an effect of absorption from the second signal.

Clause 34: The method of Clauses 22-33, wherein said determining the isolated Raman signal is based at least in part on the first signal.

Clause 35: The method of Clauses 22-34, further comprising determining a path length associated with the tissue site based at least in part on the first signal, wherein said determining the physiological parameter is based at least in part on the determined path length.

Clause 36: The method of Clauses 22-35, further comprising determining an absorption of light of the tissue site based at least in part on the second signal, wherein said determining the physiological parameter is based at least in part on the determined absorption of light.

Clause 37: The method of Clauses 22-36, wherein physiological parameter comprises a concentration of one or more analytes.

Clause 38: The method of Clauses 22-37, wherein physiological parameter comprises a blood glucose concentration associated with the tissue site.

Clause 39: The method of Clauses 22-38, further comprising calibrating the second non-invasive sensing device based at least in part on the first signal.

Clause 40: The method of Clauses 22-39, wherein second non-invasive sensing device comprises a Raman spectrometer, the method further comprising calibrating the Raman spectrometer by selecting at least one of a focal depth, a focal length, a wavelength, or a refractive index, associated with the Raman spectrometer.

Clause 41: The method of Clauses 22-40, wherein the tissue site comprises a thenar space of a hand.

Clause 42: The method of Clauses 22-41, wherein the tissue site comprises an area associated with a metacarpal bone.

Clause 43: A physiological monitoring device comprising any of the features of any of the previous clauses.

Terminology

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figures. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A physiological monitoring system configured to determine a physiological parameter by harmonizing data between two or more different types of non-invasive physiological sensors interrogating a shared tissue volume, the physiological monitoring system comprising:
   a plethysmography sensor configured to generate a first signal indicative of first physiological data associated with a shared tissue volume;
   a second non-invasive sensing device configured to generate a second signal indicative of tissue geometry data associated with the shared tissue volume, wherein the second non-invasive sensing device comprises at least one of, an optical coherence tomography (OCT) sensor, a tissue dielectric constant sensor, or a bioimpedance sensor; and one or more processors in communication with the plethysmography sensor and the second non-invasive sensing device, the one or more processors configured to:
- receive the first signal and the second signal,
- determine a physiological parameter based at least in part on the first signal and the second signal, and
- output a visual or audible indication of the physiological parameter.

2. The system of claim 1, wherein tissue geometry data comprises information related to a thickness of one or more layers of skin of the shared tissue volume, a cellular structure of the shared tissue volume, or a water content of the shared tissue volume.

3. The system of claim 1, wherein the plethysmography sensor and the second non-invasive sensing device concurrently interrogate the shared tissue volume.

4. The system of claim 1, wherein the plethysmography sensor and the second non-invasive sensing device interrogate the shared tissue volume at distinct and different time periods.

5. The system of claim 1, further comprising a Raman spectrometer configured to generate a third signal corresponding to Raman spectra associated with the shared tissue volume.

6. The system of claim 5, wherein the one or more processors are further configured to determine an isolated Raman signal by reducing or removing at least one of an effect of fluorescence or an effect of absorption from the third signal.

7. The system of claim 1, wherein the one or more processors are further configured to determine a path length associated with the shared tissue volume, wherein the physiological parameter is determined based at least in part on the path length associated with the shared tissue volume.

8. The system of claim 1, wherein the one or more processors are further configured to determine an absorption of light of the shared tissue volume, wherein the physiological parameter is determined based at least in part on the absorption of light of the shared tissue volume.

9. The system of claim 1, wherein the physiological parameter comprises a blood glucose concentration associated with the shared tissue volume.

10. The system of claim 1, further comprising a Raman spectrometer, wherein the one or more processors are further configured to calibrate the Raman spectrometer based at least in part on the first signal, wherein to calibrate the Raman spectrometer, the one or more processors are configured to select at least one of a focal depth, a focal length, a wavelength, or a refractive index, associated with the Raman spectrometer.

11. A method for determining a physiological parameter by harmonizing data between two or more different types of non-invasive physiological sensors interrogating a shared tissue volume, the method comprising:
- receiving a first signal from a plethysmography sensor configured to interrogate a shared tissue volume and generate the first signal, wherein the first signal is indicative of first physiological data associated with the shared tissue volume;
- receiving a second signal from a bioimpedance sensor, wherein the second signal is indicative of second physiological data associated with the shared tissue volume;
- determining a physiological parameter based at least in part on the first and second signals; and
- outputting a visual or audible indication of the physiological parameter.

12. The method of claim 11, wherein the plethysmography sensor and the bioimpedance sensor concurrently interrogate the shared tissue volume.

13. The method of claim 11, further comprising receiving a third signal from a tissue dielectric constant sensor, wherein the third signal is indicative of third physiological data associated with the shared tissue volume, and wherein said determining the physiological parameter is further based at least in part on the third signal.

14. The method of claim 11, further comprising receiving a third signal from a Raman spectrometer, wherein the third signal is indicative of third physiological data associated with the shared tissue volume, and wherein said determining the physiological parameter is further based at least in part on the third signal.

15. A physiological monitoring system configured to determine a physiological parameter by harmonizing data between two or more different types of non-invasive physiological sensors interrogating a shared volume of tissue, the physiological monitoring system comprising:
- a plurality of sensors configured to interrogate a shared volume of tissue of a patient, wherein each of the plurality of sensors is configured to generate a sensor signal associated with physiological data of the shared volume of tissue, wherein the plurality of sensors comprises a plethysmography sensor and a bioimpedance sensor; and
- a processor in communication with each of the plurality of sensors and configured to:
  - receive the plurality of sensor signals,
  - determine a physiological parameter associated with the shared volume of tissue based at least in part on the plurality of sensor signals, and
  - output a visual or audible indication of the physiological parameter.

16. The system of claim 13, wherein the plurality of sensors further comprises a temperature sensor, a Raman sensor, an optical coherence tomography (OCT) sensor, and a tissue dielectric constant sensor.

17. The system of claim 13, wherein the plurality of sensors comprises at least four different types of sensors.

18. The system of claim 13, wherein at least two of the plurality of sensors are configured to concurrently interrogate the shared tissue volume.

19. The system of claim 13, wherein each of the plurality of sensors is configured to interrogate the shared tissue volume at a distinct and different time period.

20. A physiological monitoring system configured to determine a physiological parameter by harmonizing data between two or more different types of non-invasive physiological sensors interrogating a shared tissue volume, the physiological monitoring system comprising:
- a plethysmography sensor configured to generate a first signal indicative of first physiological data associated with a shared tissue volume;
- a second non-invasive sensing device configured to generate a second signal indicative of second physiological data associated with the shared tissue volume, wherein the second non-invasive sensing device comprises a Raman sensor; and
- one or more processors in communication with the plethysmography sensor and the second non-invasive sensing device, the one or more processors configured to:

receive the first signal and the second signal,
determine a physiological parameter based at least in part on the first signal and the second signal, and
output a visual or audible indication of the physiological parameter.

21. The system of claim 20, wherein the one or more processors are further configured to calibrate the Raman sensor based at least in part on the first signal, wherein to calibrate the Raman sensor, the one or more processors are configured to select at least one of a focal depth, a focal length, a wavelength, or a refractive index associated with the Raman sensor.

22. The system of claim 20, wherein the one or more processors are further configured to determine an isolated Raman signal by reducing or removing at least one of an effect of fluorescence or an effect of absorption from the second signal.

* * * * *